(12) United States Patent
Unger et al.

(10) Patent No.: US 8,101,754 B2
(45) Date of Patent: *Jan. 24, 2012

(54) TRIAZOLE COMPOUNDS SUITABLE FOR TREATING DISORDERS THAT RESPOND TO MODULATION OF THE DOPAMINE $D_3$ RECEPTOR

(75) Inventors: Liliane Unger, Ludwigshafen (DE); Andreas Haupt, Schwetzingen (DE); Armin Beyerbach, Bad Dürkheim (DE); Karla Drescher, Dossenheim (DE); Wilfried Braje, Mannheim (DE); John Darbyshire, Basel (CH); Sean C. Turner, Mannheim (DE); Gisela Backfisch, Dossenheim (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/792,596

(22) PCT Filed: Dec. 1, 2005

(86) PCT No.: PCT/EP2005/012856
§ 371 (c)(1),
(2), (4) Date: Mar. 27, 2008

(87) PCT Pub. No.: WO2006/058753
PCT Pub. Date: Jun. 8, 2006

(65) Prior Publication Data
US 2008/0171751 A1    Jul. 17, 2008

Related U.S. Application Data

(60) Provisional application No. 60/632,412, filed on Dec. 2, 2004.

(51) Int. Cl.
C07D 403/14 (2006.01)
C07D 403/12 (2006.01)
A61K 31/506 (2006.01)
A61P 25/18 (2006.01)

(52) U.S. Cl. .................................. 544/327; 514/252.19

(58) Field of Classification Search .................. 544/327; 514/252.19
See application file for complete search history.

(56) References Cited

U.S. PATENT DOCUMENTS

| | | | | |
|---|---|---|---|---|
| 6,124,294 A | * | 9/2000 | Hellendahl et al. | 514/252.19 |
| 6,403,593 B1 | * | 6/2002 | Hellendahl et al. | 514/254.05 |
| 6,472,392 B1 | * | 10/2002 | Starck et al. | 514/245 |
| 6,919,342 B2 | * | 7/2005 | Haupt et al. | 514/252.19 |

FOREIGN PATENT DOCUMENTS

| | | |
|---|---|---|
| EP | 1 484 330 | 12/2004 |
| WO | WO 96/02520 A1 | 2/1996 |
| WO | WO 99/02503 | 1/1999 |
| WO | WO 00/42036 | 7/2000 |
| WO | WO 00/42037 | 7/2000 |
| WO | WO 00/42038 | 7/2000 |
| WO | WO 03/099792 | 12/2003 |
| WO | WO 2006/009765 | 1/2006 |

OTHER PUBLICATIONS

Strange, PG., et al., Trends in Pharmacological Sciences, vol. 29, No. 6, 314-321, 2008.*
Joyce et al., Drug Discovery Today, vol. 10, No. 13, 917-925, 2005.*
J.C. Schwartz et al., The Dopamine $D_3$ Receptor as a Target for Antipsychotics, in Novel Antipsychotic Drugs, H.Y. Meltzer, Ed. Raven Press, New York, 1992, pp. 135-144.
M. Dooley et al., "Pramipexole, A Review of its Use in the Management of Early and Advanced Parkinson's Disease"; Drugs and Aging 1998, 12, 495-514.
J. N. Joyce, Pharmacology and Therapeutics 2001, 90, pp. 231-259 "The Dopamine $D_3$ Receptor as a Therapeutic Target for Antipsychotic and Antiparkinsonian Drugs".
P. Sokoloff et al., Localization and Function of the $D_3$ Dopamine Receptor, Arzneim. Frosch./Drug Res. 42(1), 224 (1992).
P. Sokoloff et al., Molecular Cloning and Characterization of a Novel Dopamine Receptor ($D_3$) as a Target for Neuroleptics, Nature, 347, 146 (1990).

* cited by examiner

Primary Examiner — Venkataraman Balasubramanian
(74) Attorney, Agent, or Firm — Lisa V. Mueller; Michael Best & Friedrich LLP

(57) ABSTRACT

The invention relates to compounds of the formula I:

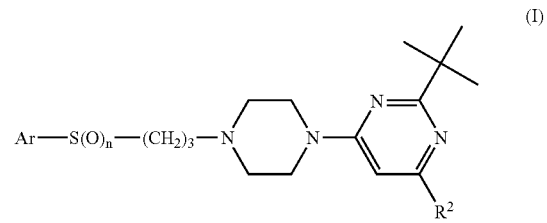

wherein
n is 1 or 2,
Ar is a C-bound 1,2,4-triazol radical which carries a radical $R^1$ on the remaining carbon atom and a radical $R^{1a}$ on one of the nitrogen atoms;
$R^1$ is hydrogen, $C_1$-$C_6$ alkyl, $C_3$-$C_6$ cycloalkyl, $C_1$-$C_4$ alkoxymethyl, fluorinated $C_1$-$C_6$ alkyl, fluorinated $C_3$-$C_6$ cycloalkyl, fluorinated $C_1$-$C_4$ alkoxymethyl, or optionially substituted phenyl or 5- or 6-membered heteroaryl;
$R^{1a}$ is hydrogen or $C_1$-$C_4$ alkyl; and
$R^2$ is $C_1$-$C_6$ alkyl, $C_3$-$C_6$ cycloalkyl, fluorinated $C_1$-$C_6$ alkyl or fluorinated $C_3$-$C_6$ cycloalkyl;
and to the physiologically tolerated acid addition salts of these compounds.
The invention also relates to a pharmaceutical composition that comprises at least one triazole compound of the formula I and/or at least one physiologically tolerated acid addition salt thereof, and further to a method for treating disorders that respond beneficially to dopamine $D_3$ receptor antagonists or dopamine $D_3$ agonists, said method comprising administering an effective amount of at least one triazole compound or physiologically tolerated acid addition salt of the formula I to a subject in need thereof.

21 Claims, No Drawings

TRIAZOLE COMPOUNDS SUITABLE FOR TREATING DISORDERS THAT RESPOND TO MODULATION OF THE DOPAMINE $D_3$ RECEPTOR

BACKGROUND OF THE INVENTION

The present invention relates to novel triazole compounds. The compounds possess valuable therapeutic properties and are suitable, in particular, for treating diseases that respond to modulation of the dopamine $D_3$ receptor.

Neurons obtain their information by way of G protein-coupled receptors, inter alia. A large number of substances exert their effect by way of these receptors. One of them is dopamine. Confirmed findings exist with regard to the presence of dopamine and its physiological function as a neurotransmitter. Disorders in the dopaminergic transmitter system result in diseases of the central nervous system which include, for example, schizophrenia, depression and Parkinson's disease. These diseases, and others, are treated with drugs which interact with the dopamine receptors.

Up until 1990, two subtypes of dopamine receptor had been clearly defined pharmacologically, termed $D_1$ and $D_2$ receptors. More recently, a third subtype was found, namely, the $D_3$ receptor which appears to mediate some effects of antipsychotics and antiparkinsonians (J. C. Schwartz et al., "The Dopamine $D_3$ Receptor as a Target for Antipsychotics" in Novel Antipsychotic Drugs, H. Y. Meltzer, ed., Raven Press, New York 1992, pages 135-144; M. Dooley et al., Drugs and Aging 1998, 12:495-514; J. N. Joyce, Pharmacology and Therapeutics 2001, 90:231-59, "The Dopamine $D_3$ Receptor as a Therapeutic Target for Antipsychotic and Antiparkinsonian Drugs"). Since then, the dopamine receptors have been divided into two families. On the one hand, there is the $D_2$ group, consisting of $D_2$, $D_3$ and $D_4$ receptors, and, on the other hand, the $D_1$ group, consisting of $D_1$ and $D_5$ receptors.

Whereas $D_1$ and $D_2$ receptors are widely distributed, $D_3$ receptors appear to be expressed regioselectively. Thus, these receptors are preferentially to be found in the limbic system and the projection regions of the mesolimbic dopamine system, especially in the nucleus accumbens, but also in other regions, such as the amygdala. Because of this comparatively regioselective expression, $D_3$ receptors are regarded as being a target having few side-effects and it is assumed that while a selective $D_3$ ligand would have the properties of known antipsychotics, it would not have their dopamine $D_2$ receptor-mediated neurological side-effects (P. Sokoloff et al., Arzneim. Forsch./Drug Res. 42(1):224 (1992), "Localization and Function of the $D_3$ Dopamine Receptor"; P. Sokoloff et al., Nature, 347:146 (1990), "Molecular Cloning and Characterization of a Novel Dopamine Receptor ($D_3$) as a Target for Neuroleptics").

Triazole compounds having an affinity for the dopamine $D_3$ receptor have been described previously on various occasions, as for example in published PCT applications WO 96/02520, WO 99/02503, WO 00/42036, WO 00/42037, WO 00/42038. Some of these compounds possess high affinities for the dopamine $D_3$ receptor, and have therefore been proposed as being suitable for treating diseases of the central nervous system. Unfortunately, their selectivity towards the $D_3$ receptor is not always satisfactory. Moreover, it has often been difficult to achieve high brain levels with such known compounds. Consequently there is an ongoing need to provide new compounds, which either have an improved selectivity towards $D_3$ receptors or an improved pharmacological profile, such as a higher brain plasma ratio, a higher bioavailability, favourable metabolic behaviour such as a decreased inhibition of the mitochondrial respiration and favourable profile regarding their interaction with cytochrome P450 isoenzymes.

SUMMARY OF THE INVENTION

It has now been found that certain triazole compounds exhibit, to a surprising and unexpected degree, highly selective binding to the dopamine $D_3$ receptor as well as the ability to attain high brain levels. Such compounds are those having the general formula I

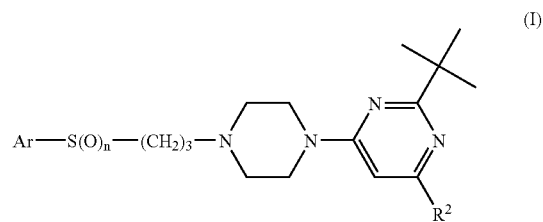

wherein
n is 1 or 2,
Ar is a C-bound 1,2,4-triazol radical which carries a radical $R^1$ on the remaining carbon atom and a radical $R^{1a}$ on one of the nitrogen atoms; wherein
$R^1$ is hydrogen, $C_1$-$C_6$ alkyl, $C_3$-$C_6$ cycloalkyl, $C_1$-$C_4$ alkoxymethyl, fluorinated $C_1$-$C_6$ alkyl, fluorinated $C_3$-$C_6$ cycloalkyl, fluorinated $C_1$-$C_4$ alkoxymethyl, phenyl or 5- or 6-membered heteroaryl, wherein phenyl and heteroaryl may be un-substituted or substituted by 1, 2, 3 or 4 radicals $R^a$ selected independently of each other from halogen, $C_1$-$C_6$ alkyl, $C_3$-$C_6$ cycloalkyl, $C_1$-$C_4$ alkoxy-$C_1$-$C_4$-alkyl, fluorinated $C_1$-$C_4$ alkyl, CN, $NO_2$, $OR^3$, $NR^3R^4$, C(O)$NR^3R^4$, O—C(O)$NR^3R^4$, $SO_2NR^3R^4$, $COOR^5$, $SR^6$, $SOR^6$, $SO_2R^6$, O—C(O)$R^7$, $COR^7$ or $C_3$-$C_5$ cycloalkylmethyl, wherein phenyl and heteroaryl may also carry a phenyl group or an aromatic 5- or 6-membered C-bound heteroaromatic radical, comprising 1 nitrogen atom as ring member and 0, 1, 2 or 3 further heteroatoms, independently of each other, selected from O, S and N, wherein the last two mentioned radicals may carry 1, 2, 3 or 4 of the aforementioned radicals $R^a$
$R^{1a}$ is hydrogen or $C_1$-$C_4$-alkyl
$R^2$ is $C_1$-$C_6$ alkyl, $C_3$-$C_6$ cycloalkyl, fluorinated $C_1$-$C_6$ alkyl or fluorinated $C_3$-$C_6$ cycloalkyl
$R^3$, $R^4$, $R^5$, $R^6$, and $R^7$ independent of each other are H, $C_1$-$C_6$ alkyl, optionally substituted with OH, $C_1$-$C_4$ alkoxy or phenyl, $C_1$-$C_4$ haloalkyl or phenyl, which may carry 1, 2 or 3 radicals selected from the group consisting of $C_1$-$C_6$ alkyl, $C_1$-$C_6$ alkoxy, $NR^{3a}R^{4a}$, CN, $C_1$-$C_2$ fluoroalkyl and halogen, wherein $R^{3a}$ and $R^{4a}$ are independent of each other H, $C_1$-$C_6$ alkyl, optionally substituted with OH, $C_1$-$C_4$ alkoxy or phenyl, $C_1$-$C_4$ haloalkyl or phenyl, which may carry 1, 2 or 3 radicals selected from the group consisting of $C_1$-$C_6$ alkyl, $C_1$-$C_6$ alkoxy, amino, NH($C_1$-$C_4$ alkyl) and N($C_1$-$C_4$ alkyl)$_2$, $R^4$ may also be a radical $COR^8$, wherein $R^8$ is hydrogen, $C_1$-$C_6$ alkyl, $C_1$-$C_6$ alkoxy or phenyl, which may carry 1, 2 or 3 radicals selected from the group consisting of $C_1$-$C_6$ alkyl, $C_1$-$C_6$ alkoxy, $NR^3R^4$, CN, $C_1$-$C_2$ fluoroalkyl and halogen, $R^3$ and $R^4$ may together with the nitrogen atom to which they are bound form a N-bound 5 or 6 membered saturated heterocyle, which may comprise an oxygen atom or an additional nitrogen atom as a ring member and which may carry 1, 2, 3 or 4 $C_1$-$C_6$ alkyl groups
and the physiologically tolerated acid addition salts of these compounds.

The present invention therefore relates to triazole compounds of the general formula I and to their physiologically tolerated acid addition salts.

The present invention also relates to a pharmaceutical composition which comprises at least one triazole compound of the formula I and/or at least one physiologically tolerated acid addition salt of I, where appropriate together with physiologically acceptable carriers and/or auxiliary substances.

The present invention also relates to a method for treating disorders which respond to influencing by dopamine $D_3$ receptor antagonists or dopamine $D_3$ agonists, said method comprising administering an effective amount of at least one triazole compound of the formula I and/or at least one physiologically tolerated acid addition salt of I to a subject in need thereof.

DETAILED DESCRIPTION OF THE INVENTION

The diseases which respond to the influence of dopamine $D_3$ receptor antagonists or agonists include disorders and diseases of the central nervous system, in particular affective disturbances, neurotic disturbances, stress disturbances and somatoform disturbances and psychoses, and especially schizophrenia, depression, bipolar disorder, substance abuse, dementia, major depressive disorder, anxiety, autism, attention deficit disorder with or without hyperactivity and personality disorder. In addition, $D_3$-mediated diseases may include disturbances of kidney function, in particular kidney function disturbances which are caused by diabetes mellitus (see WO 00/67847).

According to the invention, one or more compounds of the general formula I having the meanings mentioned at the outset can be used for treating the above-mentioned indications. Provided the compounds of the formula I possess one or more centers of asymmetry, it is also possible to use enantiomeric mixtures, in particular racemates, diastereomeric mixtures and tautomeric mixtures; preferred, however, are the respective essentially pure enantiomers, diastereomers and tautomers.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, nitric acid, sulfuric acid, organic sulfonic acids having from 1 to 12 carbon atoms, e.g. $C_1$-$C_4$-alkylsulfonic acids such as methanesulfonic acid, cycloaliphatic sulfonic acids such as S-(+)-10-camphorsulfonic acids and aromatic sulfonic acids such as benzenesulfonic acid and toluenesulfonic acid, di- and tricarboxylic acids and hydroxycarboxylic acids having from 2 to 10 carbon atoms such as oxalic acid, malonic acid, maleic acid, fumaric acid, mucic acid, lactic acid, tartaric acid, citric acid, glycolic acid and adipic acid, as well as cis- and trans-cinnamic acid, furoic acid and benzoic acid. Other utilizable acids are described in Fortschritte der Arzneimittelforschung [Advances in Drug Research], Volume 10, pages 224 ff., Birkhäuser Verlag, Basel and Stuttgart, 1966. The physiologically tolerated salts of compounds of the formula I may be present as the mono-, bis-, tris- and tetrakis-salts, that is, they may contain 1, 2, 3 or 4 of the aforementioned acid molecules per molecule of formula I. The acid molecules may be present in their acidic form or as an anion.

As used herein, $C_1$-$C_6$ alkyl is a straight-chain or branched alkyl group having 1, 2, 3, 4, 5 or 6 carbon atoms. Examples of such a group are methyl, ethyl, n-propyl, isopropyl, n-butyl, 2-butyl, isobutyl, tert-butyl, n-pentyl, 1-methylbutyl, 2-methylbutyl, 1-ethylpropyl, n-hexyl.

As used herein "5- or 6-membered aromatic radicals" comprise monocyclic aromatic radicals which comprise 1, 2, 3 or 4 heteroatoms as ring members which are selected, independently of each other from O, S and N. Examples are pyridinyl, pyrimidinyl, pyrazinyl, triazinyl, imidazolyl, pyrrolyl, pyrazolyl, thienyl, furanyl, oxazolyl, thiazolyl, isoxazolyl, tetrazolyl, thiadiazolyl and triazolyl.

A first embodiment of the invention relates to compounds of the formula I, wherein Ar is a radical of the formula Ar-1,

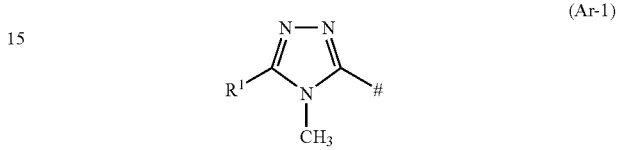

(Ar-1)

wherein # denotes the binding position to the sulfur atom of the group $S(O)_n$ and wherein $R^1$ is as defined herein.

A second embodiment of the invention relates to compounds of the formula I, wherein Ar is a radical of the formula Ar-2

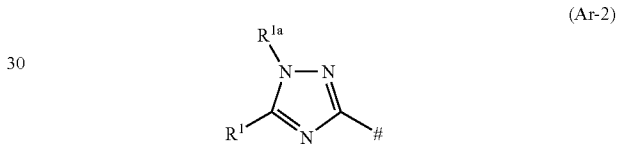

(Ar-2)

wherein # denotes the binding position to the sulfur atom of the group $S(O)_n$ and wherein $R^1$ and $R^{1a}$ are as defined herein.

A third embodiment of the invention relates to compounds of the formula I, wherein Ar is a radical of the formula Ar-3

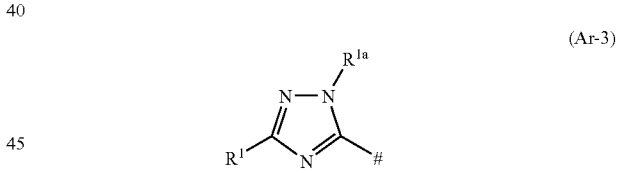

(Ar-3)

wherein # denotes the binding position to the sulfur atom of the group $S(O)^n$ and wherein $R^1$ and $R^{1a}$ are as defined herein.

$R^{1a}$ is preferably hydrogen or methyl, in particular methyl.

With regard to using the compounds according to the invention as dopamine $D_3$ receptor ligands, preference is given to those compounds of formula I in which the radical $R^1$ is hydrogen, $C_1$-$C_4$ alkyl, $C_3$-$C_5$ cycloalkyl, $C_1$-$C_4$ alkoxymethyl or trifluoromethyl, in particular hydrogen, $C_1$-$C_4$ alkyl, cyclopropyl, cyclobutyl, $CH_2$—$OCH_3$, $CH_2$—$OCH_2H_5$ or trifluoromethyl, especially methyl, ethyl, n-propyl, isopropyl, cyclopropyl, cyclobutyl, tert-butyl or trifluoromethyl and most preferably hydrogen or methyl.

$R^2$ is preferably $C_3$-$C_4$ alkyl or fluorinated $C_1$-$C_2$ alkyl, in particular n-propyl, isopropyl or tert-butyl, or alternatively trifluoromethyl or difluoromethyl. More preferable are compounds in which $R^2$ is tert-butyl, difluoromethyl or trifluoromethyl, and most preferred are those in which $R^2$ is tert-butyl. Preferred compounds of the formula I may also carry $C_3$-$C_4$ cycloalkyl or fluorinated $C_3$-$C_4$ cycloalkyl as a radical $R^2$.

In another embodiment R$^1$ is optionally substituted phenyl or optionally substituted 5- or 6-membered hetaryl, which may be unsubstituted or substituted as mentioned above. Preferred substituents on phenyl and 5- or 6-membered heteroaryl comprise halogen, in particular fluorine or chlorine, C$_1$-C$_4$ alkyl, C$_1$-C$_4$ alkoxy, flurinated C$_1$-C$_2$ alkyl, and fluorinated C$_1$-C$_2$ alkoxy. Preferably the number of substituents is 0, 1 or 2. Amongst the aromatic radicals preference is given to phenyl, thienyl and pyrrolyl, which are unsubstituted or substituted as mentioned above. Examples for suitable radicals comprise phenyl, 2-, 3- and 4-fluorophenyl, 2- and 3-thienyl and 1-methyl-pyrrol-2-yl.

The compounds of the present invention can e.g. be prepared from the corresponding sulfanyl precursors of the formula II

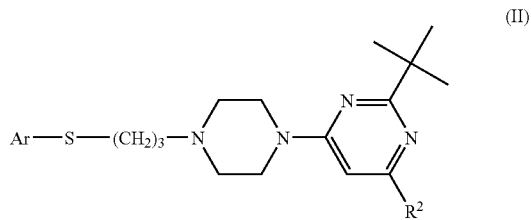

(II)

wherein Ar and R$^2$ are as defined above, via oxidation of the thioether moiety whereby the sulfinyl-derivatives Ia (n=1) and/or the sulfonyl derivatives Ib (n=2) are obtained, depending on the amount of oxidizing agent or the reaction conditions (see scheme 1). Suitable oxidizing reagents comprise peracids such as metachloroperbenzoic acid (mCPBA) (for reaction conditions see e.g. Tetrahedron Lett., 2001, 42 (46), 8161), periodates such as sodium periodate (for reaction conditions see e.g. Can. J. Chem., 2001, 79, (8), 1238), organic peroxides and inorganic peroxides such as tert-butyl-hydroperoxide, hydrogenperoxide (for reaction conditions see e.g. J. Heterocycl. Chem., 2001, 38 (5), 1035), oxone (for reaction conditions see e.g. Bioorg. Med. Chem. Lett., 2001, 11, (20), 2723), magnesium monoperoxophthalate (for reaction conditions see e.g. Synthesis, 2001, 12, 1778), and the like, with oxone being preferred.

The chiral sulfinyl derivatives Ia are also accessible via enantioselective oxidation using e.g. diethyl-tartrate/tert-butyl-hydroperoxide/titan-tetraisopropoxide as described in (i) J. Med. Chem., 2002, 45, 3972, hydrogenperoxide with chiral ligands bound to a solid support (see e.g. Chem. Commun. 2001, 24, 2594), hydrogen peroxide in combination with a vanadate-based catalyst and (1S,2R)—N-(1-(2-biphenylyl)-2-OH-3-naphthylmethylidene)-1-amino-2-indanol as chiral ligand (see e.g. Synlett., 2002, 1, 161), 1-(2-furyl)-1-methylethyl hydroperoxide/titanium tetraisopropoxide in the presence of (R)- or (S)-binol (see e.g. Tetrahedron: Asymmetry, 2001, 12 (20), 2775), or (S,S)- or (R,R)-diethyl tartrate/titanium tetraisopropoxide/cumene hydroperoxide (see e.g. Nature Reviews in Drug Discovery, 2003, 663).

Some of the compounds of the general formula II, namely the compounds of the formula II, wherein R$^1$ is selected from the group consisting of C$_2$-C$_6$-alkyl, flurorinated C$_1$-C$_6$-alkyl, C$_3$-C$_6$ cycloalkyl, C$_1$-C$_4$ alkoxymethyl, fluorinated C$_3$-C$_6$ cycloalkyl and fluorinated C$_1$-C$_4$ alkoxymethyl and R$^2$ is selected from the group consisting of C$_1$-C$_6$ alkyl and fluorinated C$_1$-C$_6$ alkyl and the physiologically tolerated acid addition salts of these compounds are new and thus form part of the invention. They are hereinafter referred to as compounds IIa.

A fourth embodiment of the invention relates to compounds of the formula IIa, wherein Ar is Ar-1 as defined above.

A fifth embodiment of the invention relates to compounds of the formula IIa, wherein Ar is Ar-2 as defined above.

A sixth embodiment of the invention relates to compounds of the formula IIa, wherein Ar is Ar-3 as defined above.

The new compounds of the formula II (compounds IIa) and their physiologically tolerated acid addition salts are highly selective towards the dopamine D$_3$ receptor and provide a similar beneficial pharmacological profile as the compounds I of the invention. Therefore compounds IIa are useful for treating disorders which respond to influencing by dopamine D$_3$ receptor ligands, such as dopamine D$_3$ receptor antagonists or dopamine D$_3$ agonists.

Therefore, the present invention also relates to a pharmaceutical composition which comprises at least one triazole Scheme 1:

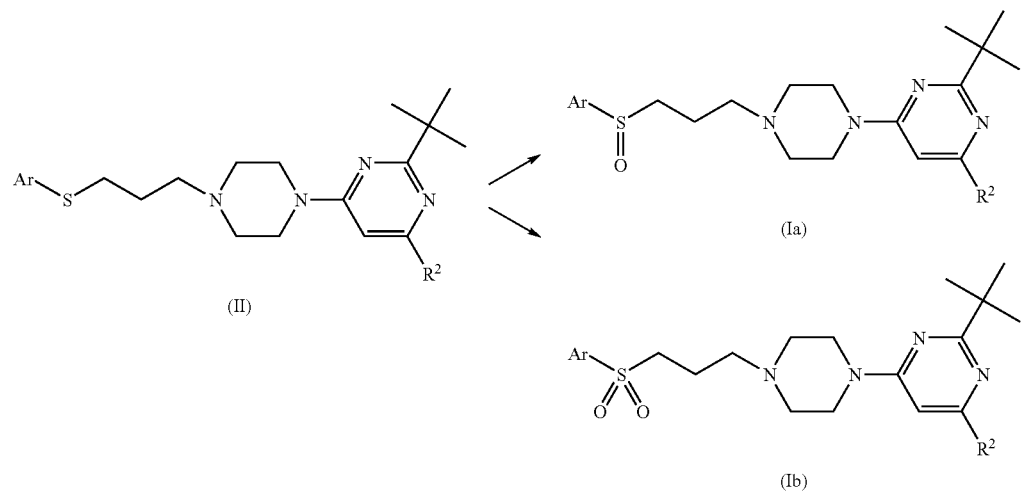

compound IIa and/or at least one physiologically tolerated acid addition salt of IIa, where appropriate together with physiologically acceptable carriers and/or auxiliary substances.

The present invention also relates to a method for treating disorders which respond to influencing by dopamine $D_3$ receptor antagonists or dopamine $D_3$ agonists, said method comprising administering an effective amount of at least one triazole compound of the formula IIa and/or at least one physiologically tolerated acid addition salt of IIa to a subject in need thereof.

In the new compounds of formula IIa $R^1$ is preferably $C_2$-$C_4$-alkyl, trifluoromethyl, $C_3$-$C_5$ cycloalkyl or $C_1$-$C_4$ alkoxymethyl, in particular ethyl, n-propyl, isopropyl, tert.-butyl, cyclopropyl, cyclobutyl, trifluoromethyl, $CH_2$—$OCH_3$ or $CH_2$—$OCH_2H_5$.

In the new compounds of formula IIa $R^2$ is preferably $C_3$-$C_4$ alkyl or fluorinated $C_1$-$C_2$ alkyl, in particular n-propyl, isopropyl or tert-butyl, or alternatively trifluoromethyl or difluoromethyl. More preferable are compounds IIa in which $R^2$ is tert-butyl, difluoromethyl or trifluoromethyl, and most preferred are those in which $R^2$ is tert-butyl.

The compounds of the formula II can be prepared in analogy to methods which are well known in the art, as for example from the international patent applications cited in the introductory part, WO 99/02503, WO 96/0250, PCT/EP2004006139 and U.S. 60/600,042. Preferred methods are outlined in schemes i) and ii) below:

Scheme i)

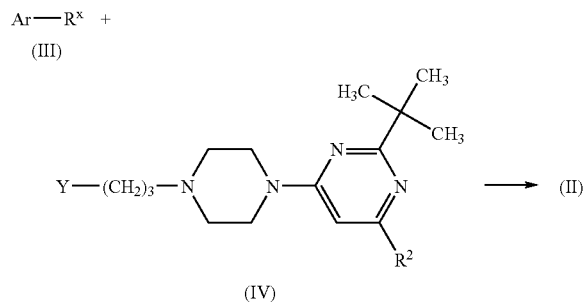

According to this scheme, a triazole of the formula III, wherein Ar is as defined above, is reacted with a piperazinylpyrimidine compound of the formula IV, wherein $R^x$ is SH and Y is a conventional leaving group such as halogen such as chlorine, bromine or iodine, alkylsulfonyloxy such as methanesulfonyloxy, arylsulfonyloxy such as phenylsulfonyloxy, or tolylsulfonyloxy (tosylate). The reaction can be performed using the conditions as described herein or in the prior art cited in the introductory part. $R^x$ may also be chlorine or bromine, while Y is SH; in this case, the reaction can be performed using the reaction conditions as described by Hester, Jackson B., Jr. and Von Voigtlander, Philip, *Journal of Medicinal Chemistry* (1979), 22(11).

Scheme ii)

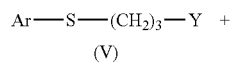

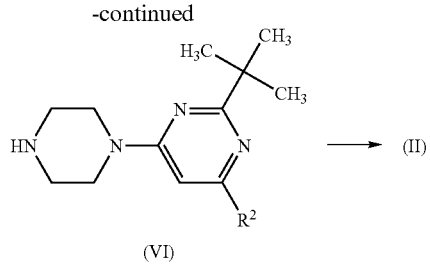

According to this scheme, a triazole of the formula V is reacted with a piperazinylpyrimidine compound of the formula VI, wherein Y is a conventional leaving group such as halogen, alkylsulfonyloxy, arylsulfonyloxy, etc as described above.

The compounds of the formulae III and V are known in the art or can be prepared according to methods described in the literature, as for example in Houben Weyl "Handbuch der Organischen Chemie", 4th Ed., Thieme Verlag, Stuttgart 1994, Volume E8/d, pages 479 et sequ.; in S. Kubota et al., *Chem. Pharm. Bull* 1975, 23:955, or in A. R. Katritzky, C. W. Rees (ed.), "Comprehensive Heterocyclic Chemistry", 1st Ed. Pergamon Press 1984, in particular Vol. 5, part 4a, pages 733 et seq. and literature cited therein; or "The Chemistry of Heterocyclic Compounds'" J. Wiley & Sons Inc. NY and literature cited therein. The compounds of the formulae III and V can be prepared according to routine methods as described for example in J. A. Kiristy et al., *J. Med. Chem.*, 21:1303 or C. B. Pollard, *J. Am. Chem. Soc.* 1934, 56:2199. Some of the triazolecompounds are commercially available Compounds of the formula III wherein Ar is Ar-1, $R^x$ is chlorine or bromine can also be prepared from compounds III with $R^x$ being OH according to the methods described by P. Viallefont et al. in *Bulletin de la Société Chimique de France* 1975, no. 3-4, 647-653, or by G. Maury et al. in *J. Heterocyclic Chemistry* 1977, 14:1311.

A preferred route to compounds of the formula IV is shown in scheme iii below:

Scheme iii)

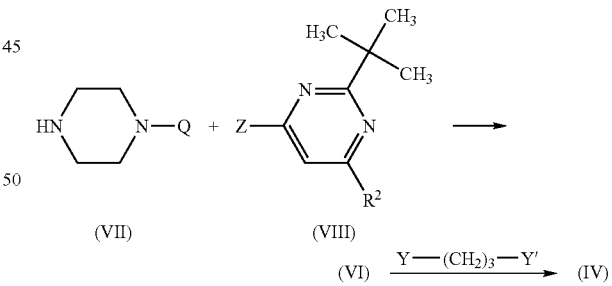

In a first step, a piperazine compound VII wherein Q is H or a protecting group for secondary amines is reacted with a pyrimidine compound VIII wherein Z is halogen to yield a compound of the formula VI. This compound is then reacted with a bifunctional propane compound Y—$(CH_2)_3$—Y', wherein Y and Y' are leaving groups of different reactivities which can be replaced by nucleophiles e.g. Y=Cl and Y'=Br. This method is known from the prior art cited in the introductory part of the application and also from WO 99/09015 and WO 03/002543. Compounds of the formula IV wherein Y is OH may also be prepared by the method disclosed in WO 03/002543.

A simple method of producing the compounds of formula III, wherein Ar is Ar-1 and $R^x$ is SH comprises the reaction of a carboxylic acid of the formula $R^1$—COOH with 4-methyl-3-thiosemicarbazide in the presence of 1,1'-carbonyldimidazole as shown in scheme iv).

Scheme iv)

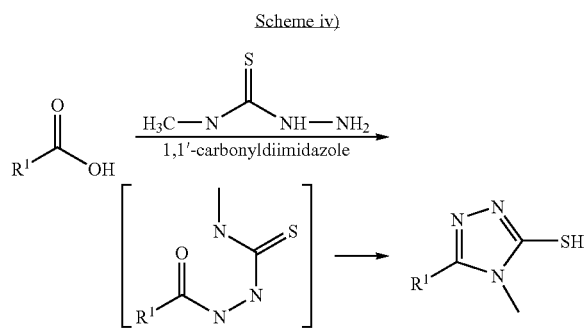

The reaction can be performed using the conditions as described herein and in El-Deen, I. M. and Ibrahim, H. K., Phosphorus, Sulfur and Silicon and the Related Elements (2002), 177(3):733-740; Faidallah et al., Phosphorus, Sulfur and Silicon and the Related Elements (2002), 177(1):67-79; Tumkevicius, Sigitas and Vainilavicius, Povilas, *Journal of Chemical Research, Synopses* (2002), 5:213-215; Palaska et al., *FABAD Journal of Pharmaceutical Sciences* (2001), 26(3):113-117; Li, Xin Zhi and Si, Zong Xing, *Chinese Chemical Letters* (2002), 13(2):129-132; and Suni et al., *Tetrahedron* (2001), 57(10):2003-2009.

The preparation of the pyrimidine compounds VIII is simply achieved by reacting tert-butylamidinium chloride with a suitable β-ketoester IX to yield a 2-tert-butyl-4-hydroxypyrimidine of the formula X which can be transformed to the halo compound VIII by reacting it with halogenating agent such as thionyl chloride, phosphoryl chloride, phosphoryl bromide, phosphorous trichloride, phosphorous tribromide or phosphorous pentachloride (see scheme v):

Scheme v)

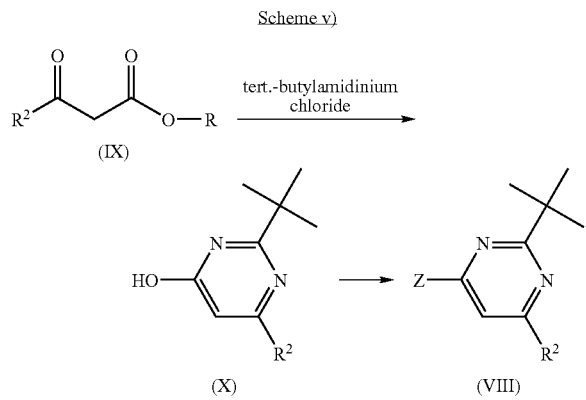

β-Ketoesters IX where $R^2$ is alkyl such as propyl, isopropyl, or tert-butyl, or trifluoromethyl are commercially available and can directly be reacted with tert-butyl-amidinium chloride, which is also commercially available from e.g. Maybridge Ltd.

β-Ketoesters where $R^2$ is fluoroalkyl such as difluoromethyl can be simply synthesized according to the methods described in this application from the corresponding acid chlorides $R^2$—COCl by reaction with meldrum's acid (2,2-dimethyl-4,6-dioxo-1,3-dioxan) according to the process as described herein and in B. Trost et al., *Journal of the American Chemical Society* (2002), 124(35):10396-10415; Paknikar, S. K. et al., *Journal of the Indian Institute of Science* (2001), 81(2):175-179; and Brummell, David G. et al., *Journal of Medicinal Chemistry* (2001), 44(1):78-93.

Compounds of the formula I (and also compounds of the formula II as defined hereinafter) wherein n is 1 contain a sulfoxide —SO— functionality which is a center of chirality. Thus, compounds of the formulae I and II can occur in the racemic form, in the (S)-form or in the (R)-form. The enantiomeric forms of these compounds can either be seperated via chiral column chromatography using chiral stationary phases like CHIRALPAK AD, CHIRALPAK OD or others, with e.g. heptane-ethanol-triethylamine mixtures of varying composition as eluent, or they can be prepared by enantioselective oxidation of the sulfanyl precursors according to e.g. the following methods described in literature or variations thereof, followed by one or more recrystallization steps (H. Kagan et al., Bull Soc Chim Fr (1996), 133, 1109-1115; F. Di Furia et al., Synthesis, 1984, 325-326; Mike S. Anson et al., Synlett 2002, 7, 1055-1060; B. Kohl et al., WO 2004/052882; F. Rebiere et al., WO 2005/028428; F. Rebiere et al., US 20050222257; S. von Unge et al., Tetrahedron: Asymmetry 11 (2000), 3819-3825, and references cited therein.

If not otherwise indicated, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see *Tetrahedron* 2001, 57, p. 9199 ff. p. 9225 ff. and also, in a general manner, "Microwaves in Organic Synthesis", André Loupy (Ed.), Wiley-VCH 2002).

Examples of solvents which can be used are ethers such as diethyl ether, diisopropyl ether, methyl tert-butyl ether or tetrahydrofuran, aprotic polar solvents such as dimethylformamide, dimethyl sulfoxide, dimethoxyethane and acetonitrile, aromatic hydrocarbons such as toluene and xylene, ketones such as acetone or methyl ethyl ketone, halohydrocarbons such as dichloromethane, trichloromethane and dichloroethane, esters such as ethyl acetate and methyl butyrate, carboxylic acids such as acetic acid or propionic acid, and alcohols such as, methanol, ethanol, n-propanol, isopropanol and butanol.

If desired, it is possible for a base to be present in order to neutralize protons which are released in the reactions. Suitable bases include inorganic bases such as sodium carbonate, potassium carbonate, sodium hydrogen carbonate or potassium hydrogen carbonate, alkoxides such as sodium methoxide or sodium ethoxide, alkali metal hydrides such as sodium hydride, organometallic compounds such as butyllithium compounds or alkylmagnesium compounds, and organic nitrogen bases such as triethylamine or pyridine. The latter compounds can at the same time serve as solvents.

The crude product is isolated in a customary manner, as for example by filtering, distilling off the solvent or extracting from the reaction mixture, etc. The resulting compounds can be purified in a customary manner, as for example by means of recrystallizing from a solvent, by means of chromatography or by means of converting into an acid addition salt.

The acid addition salts are prepared in a customary manner by mixing the free base with a corresponding acid, where appropriate in solution in an organic solvent as for example a lower alcohol such as methanol, ethanol, n-propanol or isopropanol, an ether such as methyl tert-butyl ether or diisopropyl ether, a ketone such as acetone or methyl ethyl ketone, or an ester such as ethyl acetate. For example, the free base of formula I and suitable amounts of the corresponding acid, such as from 1 to 4 moles per mol of formula I, are dissolved in a suitable solvent, preferably in a lower alcohol such as methanol, ethanol, n-propanol or isopropanol. Heating may be applied to dissolve the solids, if necessary. Solvents, wherein the acid addition salt of I is insoluble (anti-solvents), might be added to precipitate the salt. Suitable anti-solvents comprise $C_1$-$C_4$-alkylesters of $C_1$-$C_4$-aliphatic acids such as ethyl acetate, aliphatic and cycloaliphatic hydrocarbons such as hexane, cyclohexane, heptane, etc., di-$C_1$-$C_4$-alkylethers such as methyl tert-butyl ether or diisopropyl ether. A part or all of the anti-solvent may be added to the hot solution of the salt and the thus obtained solution is cooled; the remainder of the anti-solvent is then added until the concentration of the salt in the mother liquor is as low as approximately 10 mg/l or lower.

The compounds according to the invention of the formula I are surprisingly highly selective dopamine $D_3$ receptor ligands. Because of their low affinity for other receptors such as $D_1$ receptors, $D_4$ receptors, $\alpha 1$-adrenergic and/or $\alpha 2$-adrenergic receptors, muscarinergic receptors, histamine receptors, opiate receptors and, in particular, dopamine $D_2$ receptors, the compounds can be expected to give rise to fewer side-effects than do the classic neuroleptics, which are $D_2$ receptor antagonists.

The high affinity of the compounds according to the invention for $D_3$ receptors is reflected in very low in-vitro $K_i$ values of as a rule less than 60 nM (nmol/l), preferably of less than 30 nM and, in particular of less than 20 nM. The displacement of [$^{125}$I]-iodosulpride can, for example, be used in receptor binding studies for determining binding affinities for $D_3$ receptors.

The selectivity of the compounds of the invention for the $D_2$ receptor relative to the $D_3$ receptor, expressed as $K_i(D_2)/K_i(D_3)$, is as a rule at least 20, preferably at least 40. The displacement of [$^3$H]SCH23390, [$^{125}$I] iodosulpride or [$^{125}$I] spiperone can be used, for example, in carrying out receptor binding studies on $D_1$, $D_2$ and $D_4$ receptors.

Because of their binding profile, the compounds can be used for treating diseases which respond to dopamine $D_3$ ligands, that is, they can be expected to be effective for treating those medical disorders or diseases in which exerting an influence on (modulating) the dopamine $D_3$ receptors leads to an improvement in the clinical picture or to the disease being cured. Examples of these diseases are disorders or diseases of the central nervous system.

Disorders or diseases of the central nervous system are understood as meaning disorders which affect the spinal cord and, in particular, the brain. Within the meaning of the invention, the term "disorders" denotes disturbances and/or anomalies which are as a rule regarded as being pathological conditions or functions and which can manifest themselves in the form of particular signs, symptoms and/or malfunctions. While the treatment according to the invention can be directed toward individual disorders, that is, anomalies or pathological conditions, it is also possible for several anomalies, which may be causatively linked to each other, to be combined into patterns or syndromes which can be treated in accordance with the invention.

The disorders which can be treated in accordance with the invention are, in particular, psychiatric and neurological disturbances. These disturbances include, in particular, organic disturbances, including symptomatic disturbances such as psychoses of the acute exogenous reaction type or attendant psychoses of organic or exogenous cause as for example in association with metabolic disturbances, infections and endocrinopathies; endogenous psychoses such as schizophrenia and schizotype and delusional disturbances; affective disturbances such as depressions, major depressive disorder, mania and/or manic-depressive conditions; mixed forms of the above-described disturbances; neurotic and somatoform disturbances and also disturbances in association with stress; dissociative disturbances such as loss of consciousness, clouding of consciousness, double consciousness and personality disturbances; autism; disturbances in attention and waking/sleeping behavior such as behavioral disturbances and emotional disturbances whose onset lies in childhood and youth as for example hyperactivity in children, intellectual deficits such as attention disturbances (attention deficit disorders with or without hyperactivity), memory disturbances and cognitive disturbances such as impaired learning and memory (impaired cognitive function), dementia, narcolepsy and sleep disturbances such as restless legs syndrome; development disturbances; anxiety states; delirium; sexual disturbances such as impotence in men; eating disturbances such as anorexia or bulimia; addiction; bipolar disorder; and other unspecified psychiatric disturbances.

The disorders which can be treated in accordance with the invention also include Parkinson's disease and epilepsy and, in particular, the affective disturbances connected thereto.

Also treatable are addictive diseases (substance abuse), that is, psychic disorders and behavioral disturbances which are caused by the abuse of psychotropic substances such as pharmaceuticals or narcotics, and also other addiction behaviors such as addiction to gaming and/or impulse control disorders not elsewhere classified. Examples of addictive substances include opioids such as morphine, heroin and codeine: cocaine; nicotine; alcohol; substances which interact with the GABA chloride channel complex; sedatives, hypnotics and tranquilizers as for example benzodiazepines; LSD; cannabinoids; psychomotor stimulants such as 3,4-methylenedioxy-N-methylamphetamine (ecstasy); amphetamine and amphetamine-like substances such as methylphenidate; and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of dopamine $D_3$ receptors.

According to another aspect of the present invention, the treatment is directed, in particular, toward those disorders which can be influenced, within the sense of an expedient medicinal treatment, by the binding of preferably exogeneously administered binding partners (ligands) to dopamine $D_3$ receptors.

The diseases which can be treated with the compounds according to the invention are frequently characterized by progressive development, that is, the above-described conditions change over the course of time; as a rule, the severity increases and conditions may possibly merge into each other or other conditions may appear in addition to those which already exist.

The compounds according to the invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, such as Huntington's chorea and Gilles-de-la-Tourette's syndrome, vertigo syndromes such as peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, as for example for the suppression of symptoms. It can be effected over a short period, be orientated over the medium term or can be a long-term treatment, as for example within the context of a maintenance therapy.

Surprisingly, high brain levels in excess of 100 or even of 200 ng/g or even of 500 ng/g (determined in rats as the value $C_{max}$) can be achieved when administering the compounds of the invention.

Therefore the compounds according to the invention are preferentially suitable for treating diseases of the central nervous system, in particular for treating affective disorders; neurotic disturbances, stress disturbances and somatoform disturbances and psychoses, and, in particular, for treating schizophrenia and depression. Because of their high selectivity with regard to the $D_3$ receptor, the compounds I according to the invention are also suitable for treating disturbances of kidney function, in particular disturbances of kidney function which are caused by diabetes mellitus (see WO 00/67847) and, especially, diabetic nephropathy.

In addition, compounds of the present invention may possess other pharmacological and/or toxicological properties that render them especially suitable for development as pharmaceuticals. As an example, compounds of formula I having a low affinity for the HERG receptor could be expected to have a reduced likelihood of inducing QT-prolongation (regarded as a one predictor of risk of causing cardiac arrythmia. (For a discussion of QT-prolongation see for example A. Cavalli et al., *J. Med. Chem.* 2002, 45:3844-3853 and the literature cited therein; a HERG assay is commercially available from GENION Forschungsgesellschaft mbH, Hamburg, Germany).

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.01 to 1000 mg/kg, more preferably from 0.1 to 1000 mg/kg of bodyweight in the case of oral administration, or of from about 0.01 to 100 mg/kg, more preferably from 0.1 to 100 mg/kg of bodyweight in the case of parenteral administration, is supplied to an individual to be treated.

The invention also relates to the production of pharmaceutical compositions for treating an individual, preferably a mammal and in particular a human being, a farm animal or a domestic animal. Thus, the compounds are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms such as powders, granules, tablets (in particular film tablets), lozenges, sachets, cachets, sugar-coated tablets, capsules such as hard gelatin capsules and soft gelatin capsules; suppositories or vaginal medicinal forms; semisolid medicinal forms such as ointments, creams, hydrogels, pastes or plasters; and also liquid medicinal forms such as solutions, emulsions (in particular oil-in-water emulsions), suspensions such as lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are usually mixed or diluted with an excipient. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4$^{th}$ edition, Aulendorf: ECV-Editio-Kantor-Verlag, 1996.

The following examples serve to explain the invention without limiting it.

The compounds were either characterized via proton-NMR in d$_6$-dimethylsulfoxid or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

PREPARATION EXAMPLES

I. Preparation of Intermediates a. Preparation of 2-tert.butyl-pyrimidine-compounds IV a.1 2-tert-Butyl-4-[4-(3-chloro-propyl)-piperazin-1-yl]-6-cyclobutyl-pyrimidine a.1.1: Methyl-2-cyclobutanoyl-acetate 22 g of meldrum's acid (2,2-dimethyl-1,3-dioxane-4,6-dione) (152.7 mmol) and 36.9 ml of pyridine (457.2 mmol) were dissolved in 200 ml of dichloromethane. 18.1 g of cyclobutylcarbonic acid chloride were added at 0 to 10° C. The reaction mixture was stirred overnight at room temperature, washed with 1 N HCl and extracted with dichloromethane. The organic layer was washed with water, dried over magnesium sulfate, filtered, and then concentrated to dryness. The oily residue was dissolved in 300 ml of methanol and heated under reflux for 2 h. The reaction mixture was concentrated to dryness and the residue purified via silica gel chromatography with ethyl acetate as eluent. Yield: 21.2 g MS (ESI) m/z: 157.1 [M+H]$^+$ $^1$H-NMR (CDCl$_3$): δ [ppm] 3.7 (s, 3H), 3.4 (s, 2H), 3.3-3.4 (m, 1H), 2.2-2.4 (m, 2H), 2.1-2.25 (m, 2H), 1.9-2.1 (m, 1H), 1.8-1.9 (m, 1H).

a.1.2: 2-tert-Butyl-4-hydroxy-6-cyclobutyl-pyrimidine 9.2 g of tert-butyl amidinium chloride (67.3 mmol, Maybridge) and 12.6 g of methyl-2-cyclobutanoyl acetate (80.7 mmol) were dissolved/suspended in 100 ml of methanol. 14.5 g of sodium methanolate (268.4 mmol) were added in portions to the solution at 10° C. The suspension was then stirred at room temperature overnight. The reaction mixture was concentrated to roughly half the volume and filtered. The filtrate was extracted with water and dichloromethane. The organic phase was dried over magnesium sulfate, filtered, and then concentrated to dryness. The residue was stirred with acetone and the precipitate was collected by filtration. Yield: 11.9 g (85.7%).

MS (ESI) m/z: 207.2 [M+H]$^+$ a.1.3: 2-tert-Butyl-4-chloro-6-cyclobutyl-pyrimidine 9.9 g of 2-tert-butyl-4-hydroxy-6-cyclobutyl-pyrimidine (48 mmol) were dissolved in 80 ml of toluene and 1 ml of dimethylformamide. 10.7 ml of POCl$_3$ (114.8 mmol) were added dropwise at 10° C. Stirring was continued for 3 h at room temperature. The reaction mixture was poured into water, and the aqueous layer extracted with dichloromethane. The organic layer was dried over magnesium sulfate, filtered, and then concentrated to dryness to give 10.8 g of a yellowish oil (quant.).

a.1.4: 2-tert-Butyl-4-(piperazin-1-yl)-6-cyclobutyl-pyrimidine 24.8 g of piperazine (287.9 mmol) were dissolved in 350 ml of ethanol and heated to reflux. 24.9 g of 2-tert-butyl-4-chloro-6-cyclobutyl-pyrimidine (48.06 mmol), dissolved in 50 ml of ethanol, were added dropwise to the solution. The solution was refluxed for further 3 h, cooled to room temperature and then extracted with water and ethyl acetate. The organic layer was washed with 5% citric acid (aq.), and the aqueous layer was adjusted to alkaline pH with 2 N NaOH. The alkaline aqueous layer was reextracted with ethyl acetate, and the organic phase was dried over magnesium sulfate, filtered and concentrated to dryness to yield 8.6 g (65.2%) of the title compound.

MS (ESI) m/z: 275.2 [M+H]$^+$ $^1$H-NMR (CDCl$_3$): δ [ppm] 6.1 (s, 1H), 3.6 (m, 4H), 3.4 (m, 1H), 2.9 (m, 4H), 2.3 (m, 4H), 1.8-2.1 (m, 3H), 1.3 (s, 9H)

a.1.5: 2-tert-Butyl-4-[4-(3-chloro-propyl)-piperazin-1-yl]-6-cyclobutyl-pyrimidine 3.5 g of 2-tert-butyl-4-(piperazin-1-yl)-6-cyclobutyl-pyrimidine (12.75 mmol), 2.3 g of 1-bromo-3-chloro-propane (14.6 mmol) and 2.8 ml of triethylamine (20.1 mmol) were dissolved in 70 ml of dimethylformamide. The mixture was stirred at room temperature overnight and for further 3 h at 40° C. The reaction mixture was then extracted with water and ethyl acetate. The organic layer was dried over magnesium sulfate, filtered, and concentrated to dryness. The crude product was then purified by silica gel chromatography (dichloromethane as eluent) to yield 3.0 g (67%) of the title compound.

a.2 2-tert-Butyl-4-[4-(3-chloro-propyl)-piperazin-1-yl]-6-(1-methylcyclopropyl)-pyrimidine was obtained by analogy to the method outlined in a.1: MS (ESI) m/z: 351.2 [M+H]$^+$ a.3. 2-tert-Butyl-4-[4-(3-chloro-propyl)-piperazin-1-yl]-6-n-propylpyrimidine was obtained by analogy to the method outlined in a.1: MS (ESI) m/z: 339.2 [M+H]$^+$ a.4. 2-tert-Butyl-6-tert.-butyl-4-[4-(3-chloro-propyl)-piperazin-1-yl]-pyrimidine was obtained by analogy to the method outlined in a.1: MS (ESI) m/z: 353.3 [M+H]$^+$ a.5. 2-tert-Butyl-6-trifluoromethyl-4-[4-(3-chloro-propyl)-piperazin-1-yl]-pyrimidine was obtained by analogy to the method outlined in a.1.

b. Preparation of 3-mercapto-4-methyl-triazoles 111 b.1 4-Methyl-5-methyl-4H-[1,2,4]triazole-3-thiol 62.4 g of N,N'-carbonyldiimidazol (0.385 mol) were added in portions within 10 min. to a mixture of 22 g of acetic acid (0.366 mol) and 300 ml of dimethylformamide. The temperature rose from 22° C. to about 26° C. After the addition was completed, stirring was continued for 30 min. Then 38.5 g of 4-methyl-3-thiosemicarbazid (0.366 mol) and 100 ml of pyridine were added. The reaction mixture was heated to 100° C. and stirred for 4 h at this temperature. Stirring was continued for 14 h at room temperature. The solvent was evaporated under reduced pressure. The residue was treated with 200 ml of isopropanol and 150 ml of ethyl acetate, and re-dissolved at 80° C. Crystallization of the product started during cooling to room temperature. 300 ml of isopropanol were added and the obtained suspension was stirred for 1 h at room temperature. The precipitate was collected by filtration, washed twice with 75 ml of isopropanol each and dried under vacuum at 40° C. to yield 20.4 g of the title compound.

MS (ESI) m/z: 130.1 [M+H]$^+$
$^1$H-NMR (DMSO): δ [ppm] 13.4 (s, broad, 1H), 3.4 (s, 3H), 2.3 (s, 3H)

b.2. 4-Methyl-5-methoxymethyl-4H-[1,2,4]triazole-3-thiol 5 g of methoxy-acetic acid (55.5 mmol) were dissolved in 70 ml of dimethylformamide. 11.73 g of 1,1'-carbonyldiimidazol (72.3 mmol) were added in portions within 10 min. After 30 min. at room temperature 23 ml of pyridine were added. Then 5.84 g of 4-methyl-3-thiosemicarbazide (55.5 mmol) were added and the obtained solution was stirred at room temperature overnight, and for an additional 3 h at 100° C. The solvent was evaporated, the residue dissolved in 70 ml of saturated aqueous sodium chloride solution and 30 ml of water. The aqueous layer was extracted six times with 100 ml of ethyl acetate each, and the combined organic layers were dried over magnesium sulfate, filtered, and the solvent was evaporated to dryness to yield 17 g of the crude title compound, which was further purified by silica gel chromatography with ethyl acetate, thereby obtaining 7.1 g of the purified title compound.

MS (ESI) m/z: 160.1 [M+H]$^+$ b.3 5-Ethyl-4-methyl-4H-[1,2,4]triazole-3-thiol was obtained by analogy to method b.2

MS (ESI) m/z: 144.1 [M+H]$^+$ b.4 4-Methyl-5-(4-fluorophenyl)-4H-[1,2,4]triazole-3-thiol was purchased from Chembridge Corporation b.5 5-Cyclobutyl-4-methyl-4H-[1,2,4]triazole-3-thiol was obtained by analogy to method b.2: MS (ESI) m/z: 170.1 [M+H]$^+$ b.6 4-Methyl-4H-[1,2,4]triazole-3-thiol was purchased from Aldrich b.7 4-Methyl-5-phenyl-4H-[1,2,4]triazole-3-thiol was purchased from Chembridge Corporation b.8 5-Cyclopropyl-4-methyl-4H-[1,2,4]triazole-3-thiol was obtained by analogy to method b.2: MS (ESI) m/z: 156.1 [M+H]$^+$ b.9 4-Methyl-5-trifluoromethyl-4H-[1,2,4]triazole-3-thiol was purchased from Acros b.10 4-Methyl-5-(1-methylpyrrol-2-yl)-4H-[1,2,4]triazole-3-thiol was obtained by analogy to method b.2.

c: Preparation of Compounds II c.1 2-tert-Butyl-4-{4-[3-(4-methyl-4H-[1,2,4]triazol-3-ylsulfanyl)-propyl]-piperazin-1-yl}-6-cyclobutylpyrimidine 0.8 g of 2-tert-butyl-4-[4-(3-chloro-propyl)-piperazin-1-yl]-6-cyclobutyl-pyrimidine (2.28 mmol), 0.29 g of 4-methyl-3-mercapto-1,2,4-triazole (2.52 mmol), 0.15 g of lithium hydroxide and a tip of a spatula of potassium iodide were dissolved in 20 ml of dimethylformamide. The mixture was stirred for 14 h at room temperature and then extracted with water and ethyl acetate. The organic layer was dried over magnesium sulfate, filtered, and evaporated to dryness. The residue was then purified by column chromatography on silica gel (dichloromethane-methanol (2-10%)) to yield an oily residue that was precipitated with acetonitrile thereby yielding 0.46 g of the title compound (47%).

MS (ESI) m/z: 430.5 [M+H]$^+$
$^1$H-NMR (DMSO): δ [ppm] 8.1 (s, 1H), 6.1 (s, 1H), 3.15 (m, 4H), 3.1 (s, 3H), 3.4 (m, 1H), 3.3 (m, 2H), 2.45 (m, 6H), 2.25 (m, 4H), 2.0 (m, 3H), 1.9 (m, 1H), 1.3 (s, 9H).

c.2 2-tert-Butyl-4-{4-[3-(4-methyl-5-methyl-4H-[1,2,4]triazol-3-ylsulfanyl)-propyl]-piperazin-1-yl}-6-tert-butyl-pyrimidine hydrochloride 1 g of 2-tert-butyl-4-[4-(3-chloro-propyl)-piperazin-1-yl]-6-tert-butyl-pyrimidine (2.83 mmol), 0.4 g of 4-methyl-5-methyl-4H-[1,2,4]triazole-3-thiol (3.09 mmol), 0.2 g of lithium-hydroxide (8.35 mmol) and a spatula tip of potassium iodide werde stirred in 20 ml of dimethylformamide for 2 h at 80° C. After addition of water and ethyl acetate, the organic phase was separated and dried over magnesium sulfate. After filtration and evaporation of the solvent, the crude product was purified by column chromatography on silica gel using dichloromethane-methanol (1-6%). Fractions containing the product were combined and the solvent was evaporated. The residue was dissolved in isopropanol, and a solution of HCl in isopropanol was added. On addition of diisopropylethylether, the product formed an oily mass. The solvent was decanted and the remaining oil evaporated to dryness to yield 0.6 g (41%) of the title compound as a white solid.

MS (ESI) m/z: 446.3 [M+H]$^+$
$^1$H-NMR (DMSO): δ [ppm] 12.0 (s, 1H, broad), 6.8 (s, 1H, broad), 4.7 (m, 2H, broad), 3.4-3.7 (m, 4H, very broad), 3.6 (s, 3H), 3.4 (m, 2H), 3.25 (m, 2H), 3.0-3.4 (m, 2H, very broad), 2.6 (s, 3H), 2.2 (m, 2H), 1.4 (s, 18H, broad)

c.3 2-tert-Butyl-4-{4-[3-(4-methyl-5-cyclopentyl-4H-[1,2,4]triazol-3-ylsulfanyl)-propyl]-piperazin-1-yl}-6-trifluoromethyl-pyrimidine trifluoroacetate 1 g of 2-tert-butyl-4-[4-(3-chloro-propyl)-piperazin-1-yl]-6-trifluoromethyl-pyrimidine (2.74 mmol) and 0.55 g of 4-methyl-5-cyclopentyl-4H-[1,2,4]triazole-3-thiol (3.0 mmol) were dissolved in 10 ml of n-butanol. After addition of 0.197 g of lithium hydroxide (8.22 mmol) and 0.205 g of sodium iodide (1.37 mmol), the reaction mixture was heated to 79° C. for 3 h. After cooling, the solution was filtered, and the filtrate evaporated to dryness. The residue was partitioned between 30 ml of ethyl acetate, 20 ml of water and 20 ml of an aqueous saturated solution of sodium chloride. The aqueous layer was re-extracted twice with 30 ml of ethyl acetate each. The combined organic layers were dried over magnesium sulfate, filtered, and the solvent was evaporated. The residue was purified by preparative HPLC on a C18-Symmetry column (Waters). Fractions containing the product were combined and lyophilised to yield 0.25 g of the title compound.

MS (ESI) m/z: 512.3 [M+H]$^+$ $^1$H-NMR (DMSO): δ [ppm] 7.05 (s, 1H), 3.75 (m, broad, 4H), 3.5 (s, 3H), 3.2 (m, 1H), 3.15 (m, 2H), 2.45 (m, 6H), 2.05 (m, 2H), 1.85 (m, 4H), 1.75 (m, 2H), 1.65 (m, 2H), 1.3 (s, 9H)

c.4 2-tert-Butyl-4-{4-[3-(4-methyl-5-methoxymethyl-4H-[1,2,4]triazol-3-ylsulfanyl)-propyl]-piperazin-1-yl}-6-difluoromethyl-pyrimidine hydrochloride 0.6 g of 4-methyl-5-methoxymethyl-4H-[1,2,4]triazole-3-thiol (3.77 mmol), 0.09 g of lithium hydroxide (3.77 mmol) and 0.28 g sodium iodide (1.88 mmol) were dissolved in 20 ml of dimethylformamide. Within 2 h, a solution of 1.31 of g 2-tert-butyl-4-[4-(3-chloro-propyl)-piperazin-1-yl]-6-difluoromethyl-pyrimidine (3.77 mmol) in 5 ml of dimethylformamide was added at 70° C. Stirring was continued for 1 h at 80° C. After cooling, the solvent was evaporated and the remaining oily residue was partitioned between 30 ml of ethyl acetate, 15 ml of water and 15 ml of a saturated aqueous solution of sodium chloride. The aqueous layer was re-extracted twice with 20 ml ethyl acetate each and the organic layers were combined, dried over magnesium sulfate, filtered, and the solvent was evaporated. The residue was purified by column chromatography on silica gel employing in succession dichloromethane-ethyl acetate 1:1, ethyl acetate, and ethyl acetate-methanol 5:1. Fractions containing the product were combined, the solvents was evaporated and the residue was re-dissolved in 15 ml ethyl acetate. A 4 N solution of HCl in diethyl ether was added to precipitate the hydrochloride salt. The solution was decanted and the residue dried.

Yield: 0.55 g.

MS (ESI) m/z: 470.2 [M+H]$^+$ $^1$H-NMR (DMSO): δ [ppm] 11.95 (s, 1H, broad), 9.8 (s, 3H, broad), 7.0 (s, 1H), 6.8 (t, 1H, CHF2), 4.7 (s, 2H), 4.6 (m, 2H, broad), 3.45-3.7 (m, 4H, broad), 3.6 (s, 3H), 3.4 (m, 2H), 3.35 (s, 3H), 3.2 (m, 2H), 2.95-3.2 (m, 2H, broad), 2.2 (m, 2H), 1.3 (s, 9H), 1.2 (m, 1H)

c.5 2-tert-Butyl-4-{4-[3-(4-methyl-4H-[1,2,4]triazol-3-ylsulfanyl)-propyl]-piperazin-1-yl}-6-tert-butyl-pyrimidine hydrochloride 1 g of 2-tert-butyl-4-[4-(3-chloro-propyl)-piperazin-1-yl]-6-tert-butyl-pyrimidine (2.83 mmol), 0.35 g of 4-methyl-4H-[1,2,4]triazole-3-thiol (3.04 mmol), 0.2 g of lithium-hydroxide (8.35 mmol) and a spatula tip of potassium iodide were stirred for 72 h in 20 ml of dimethylformamide. Water and ethyl acetate were added and the organic layer was separated, dried over magnesium sulfate, filtered and the solvent was evaporated. The residue was subjected to a column chromatography on silica gel using dichloromethane-methanol (2-10%). Fractions containing the product were combined, the solvent was evaporated and the residue re-dissolved in isopropanol. The solution was treated with HCl/isopropanol. Diisopropylethylether was added whereby an oily precipitate formed. The solvent was decanted and the remaining oil evaporated to dryness to yield 1.1 g (77%) of the title compound as a white solid.

MS (ESI) m/z: 432.2 [M+H]$^+$ $^1$H-NMR (DMSO): δ [ppm] 12.5 (s, 1H, broad), 12.1 (s, 1H, broad), 9.65 (s, 1H), 6.85 (s, 1H), 5.0 (m, broad, 1H), 4.7 (m, broad, 1H), 3.75 (m, 1H), 3.7 (s, 3H), 3.65 (m, broad, 3H), 3.45 (m, 2H), 3.25 (m, 2H), 3.2 (m, 2H), 2.2 (m, 2H), 1.45 (m, 18H).

c.6 2-tert-Butyl-4-{4-[3-(4-methyl-5-trifluoromethyl-4H-[1,2,4]triazol-3-ylsulfanyl)-propyl]-piperazin-1-yl}-6-difluoromethyl-pyrimidine hydrochloride 0.5 g of 4-methyl-5-trifluoromethyl-4H-[1,2,4]triazole-3-thiol (2.73 mmol), 0.07 g of lithium hydroxide (2.73 mmol) and 0.2 g of sodium iodide (1.36 mmol) were dissolved in 20 ml of dimethylformamide. Within 1 h, a solution of 0.95 g of 2-tert-butyl-4-[4-(3-chloro-propyl)-piperazin-1-yl]-6-difluoromethyl-pyrimidine (2.73 mmol) in 4 ml of dimethylformamide was added at 70° C. Stirring was continued for 3 h at 70° C. After cooling, the solvent was evaporated and the remaining oily residue partitioned between 30 ml of ethyl acetate, 15 ml of water plus 10 ml of a saturated aqueous solution of sodium chloride. The aqueous layer was re-extracted twice with 15 ml of ethyl acetate each, and the combined organic layers were dried over magnesium sulfate, filtered, and the solvent was evaporated. The crude product was purified by column chromatography on silica gel using ethyl acetate. Fractions containing the product were combined, the solvent was evaporated and the residue was re-dissolved in 20 ml of ethyl acetate. A 1N solution of HCl in diethyl ether was added to precipitate the title compound as the'hydrochloride salt. The solution was cautiously evaporated to dryness to yield 0.64 g of the title compound as a white crystalline material.

MS (ESI) m/z: 494.2 [M+H]$^+$ $^1$H-NMR (DMSO): δ [ppm] 11.8 (s, 1H, broad), 7.1 (s, 1H), 6.7-7.0 (t, 1H, CHF$_2$), 3.7 (s, 2H), 3.6 (m, 4H), 3.4 (m, 2H), 3.25 (m, 2H), 3.1̄ (m, 2H), 2.2 (m, 2H), 1.3 (s, 9H), c.7 2-tert-Butyl-4-{4-[3-(4-methyl-5-tert-butyl-4H-[1,2,4]triazol-3-ylsulfanyl)-propyl]-piperazin-1-yl}-6-difluoromethyl-pyrimidine hydrochloride 1.0 g of 2-tert-butyl-4-[4-(3-chloro-propyl)-piperazin-1-yl]-6-difluoromethyl-pyrimidine (2.88 mmol), 0.5 g of 4-methyl-5-tert-butyl-4H-[1,2,4]triazole-3-thiol (2.92 mmol), 0.17 g lithium-hydroxide (7.1 mmol) and a spatula tip of potassium iodide were stirred in 30 ml of dimethylformamide for 14 h at room temperature. After addition of water and ethyl acetate, the organic layer was separated and dried over magnesium sulfate. After filtration and evaporation of the solvent, the crude product was purified by column chromatography on silica gel using dichloromethane-methanol (2%). Fractions containing the product were combined and the solvents were evaporated. The residue was dissolved in isopropanol and a solution of HCl in isopropanol was added. The thus formed precipitate was collected and dried thoroughly to yield 0.6 g (37.5%) of the title compound.

MS (ESI) m/z: 482.4 [M+H]$^+$ $^1$H-NMR (DMSO): δ [ppm] 7.0 (s, 1H), 6.8 (t, 1H, CHF2), 4.6 (m, broad, 2H), 3.8 (s, 3H), 3.55 (m, broad, 4H), 3.45 (m, 2H), 3.2 (m, 2H), 3.1 (m, 2H), 2.2 (m, 2H), 1.5 (s, 9H), 1.3 (s, 9H).

The compounds II of examples c.8 to c.29 were prepared in a similar manner as described in the examples c.1 to c.7:

c.8 2-tert-Butyl-4-{4-[3-(4-methyl-5-trifluoromethyl-4H-[1,2,4]triazol-3-ylsulfanyl)-propyl]-piperazin-1-yl}-6-tert-butyl-pyrimidine hydrochloride Reaction of 0.5 g of 2-tert-butyl-4-[4-(3-chloro-propyl)-piperazin-1-yl]-6-tert-butyl-pyrimidine (1.42 mmol) and 0.28 g of 4-methyl-5-trifluoromethyl-4H-[1,2,4]triazole-3-thiol (1.53 mmol) yielded 0.35 g (43%) of the title compound as a white solid.

MS (ESI) m/z: 500.3 [M+H]$^+$ $^1$H-NMR (DMSO): δ [ppm] 12.5 (s, 1H, broad), 12.1 (s, 1H, broad), 6.9 (s, 1H), 4.7 (m, 2H, broad), 3.85 (m, broad, 2H), 3.7 (s, 3H), 3.65 (m, 2H), 3.4 (m, 2H), 3.25 (m, 2H), 3.2 (m, 2H), 2.2 (m, 2H), 1.45 (m, 18H), c.9 2-tert-Butyl-4-{4-[3-(4-methyl-5-cyclopropyl-4H-[1,2,4]triazol-3-ylsulfanyl)-propyl]-piperazin-1-yl}-6-tert-butyl-pyrimidine hydrochloride Reaction of 0.5 g of 2-tert-butyl-4-[4-(3-chloro-propyl)-piperazin-1-yl]-6-tert-butyl-pyrimidine (1.42 mmol) with 0.22 g of 4-methyl-5-cyclopropyl-4H-[1,2,4]triazole-3-thiol (1.42 mmol) yielded 0.32 g of the title compound.

MS (ESI) m/z: 472.4 [M+H]$^+$ c.10 2-tert-Butyl-4-{4-[3-(4-methyl-5-methyl-4H-[1,2,4]triazol-3-ylsulfanyl)-propyl]-piperazin-1-yl}-6-propyl-pyrimidine hydrochloride Reaction of 1 g of 2-tert-butyl-4-[4-(3-chloro-propyl)-piperazin-1-yl]-6-propyl-pyrimidine (2.95 mmol) with 0.42 g of 4-methyl-5-methyl-4H-[1,2,4]triazole-3-thiol (3.25 mmol) yielded 0.5 g (33.6%) of title compound as a solid.

MS (ESI) m/z: 432.2 [M+H]$^+$ $^1$H-NMR (DMSO): δ [ppm] 14.4 (s, 1H, broad), 12.1 (s, 1H, broad), 7.15 (s, 1H), 5.0 (m, broad, 1H), 4.5 (s, broad, 1H), 3.75 (m, 1H), 3.7 (m, broad, 3H), 3.65 (s, 3H), 3.4 (m, 2H), 3.3 (m, 2H), 3.25 (m, broad, 2H), 2.95 (m, 2H), 2.65 (s, 3H), 2.2 (m, 2H), 1.7 (m, 2H), 1.4 (s, 9H), 0.9 (m, 3H)

c.11 2-tert-Butyl-4-{4-[3-(4-methyl-5-ethyl-4H-[1,2,4]triazol-3-ylsulfanyl)-propyl]-piperazin-1-yl}-6-propyl-pyrimidine hydrochloride Reaction of 0.3 g of 4-methyl-5-ethyl-4H-[1,2,4]triazole-3-thiol (2.09 mmol) with 0.71 g of 2-tert-butyl-4-[4-(3-chloro-propyl)-piperazin-1-yl]-6-propyl-pyrimidine (2.09 mmol) yielded 0.63 g of the title compound.

MS (ESI) m/z: 446.3 [M+H]$^+$ $^1$H-NMR (DMSO): δ [ppm] 14.25 (s, 1H, broad), 12.1 (s, 1H, broad), 7.15 (s, 1H), 5.0 (m, 1H, broad), 4.4 (m, 1H, broad), 3.0-4.0 (m, broad, 6H), 3.6 (s, 3H), 3.35 (m, 2H), 3.25 (m, 2H), 2.9 (m, 4H), 2.15 (m, 2H), 1.7 (m, 2H), 1.45 (s, 9H), 1.3 (m, 3H), 0.95 (m, 3H)

c.12 2-tert-Butyl-4-{4-[3-(4-methyl-5-methoxymethyl-4H-[1,2,4]triazol-3-ylsulfanyl)-propyl]-piperazin-1-yl}-6-propyl-pyrimidine hydrochloride 0.35 g of 4-methyl-5-methoxymethyl-4H-[1,2,4]triazole-3-thiol (2.19 mmol) were reacted with 0.75 g of 2-tert-butyl-4-[4-(3-chloro-propyl)-piperazin-1-yl]-6-propyl-pyrimidine (2.19 mmol) to yield 0.79 g of the title compound.

MS (ESI) m/z: 462.3 [M+H]$^+$ $^1$H-NMR (DMSO): δ [ppm] 14.4 (s, 1H, broad), 12.1 (s, 1H, broad), 7.9 (s, broad, 2H), 7.2 (s, 1H), 5.0 (m, 1H, broad), 4.7 (s, 3H), 4.5 (m, 1H, broad), 3.85 (m, 1H), 3.9-3.5 (m, 3H), 3.65 (s, 3H), 3.1-3.45 (m, 6H), 2.95 (m, 2H), 2.2 (m, 2H), 1.7 (m, 2H), 1.45 (s, 9H), 0.95 (m, 3H)

c.13 2-tert-Butyl-4-{4-[3-(4-methyl-5-trifluoromethyl-4H-[1,2,4]triazol-3-ylsulfanyl)-propyl]-piperazin-1-yl}-6-trifluoromethyl-pyrimidine hydrochloride 1 g of 2-tert-butyl-4-[4-(3-chloro-propyl)-piperazin-1-yl]-6-trifluoromethyl-pyrimidine (2.74 mmol) were reacted with 0.55 g of 4-methyl-5-trifluoromethyl-4H-[1,2,4]triazole-3-thiol (3 mmol) to yield 0.7 g (43.7%) of the title compound as a white solid.

MS (ESI) m/z: 512.2 [M+H]$^+$ $^1$H-NMR (DMSO): δ [ppm] 11.7 (s, 1H, broad), 7.25 (s, 1H), 4.55 (m, broad, 1H), 3.7 (s, 3H), 3.6 (m, 5H), 3.4 (m, 2H), 3.25 (m, 2H), 3.1 (m, 2H), 2.25 (m, 2H), 1.3 (s, 9H)

c.14 2-tert-Butyl-4-{4-[3-(4-methyl-5-methyl-4H-[1,2,4]triazol-3-ylsulfanyl)-propyl]-piperazin-1-yl}-6-trifluoromethyl-pyrimidine hydrochloride 3 g of 4-methyl-5-methyl-4H-[1,2,4]triazole-3-thiol (23.22 mmol) were reacted with 8.47 g of 2-tert-butyl-4-[4-(3-chloro-propyl)-piperazin-1-yl]-6-trifluoromethyl-pyrimidine (23.22 mmol) to yield 8.7 g of the title compound.

MS (ESI) m/z: 458.4 [M+H]$^+$ $^1$H-NMR (DMSO): δ [ppm] 11.9 (s, 1H, broad), 7.2 (s, 1H), 4.7 (m, 2H), 3.5-3.8 (m, 7H), 3.4 (m, 2H), 3.2 (m, 2H), 3.1 (m, 2H), 2.6 (s, 3H), 2.2 (m, 2H), 1.3 (s, 9H)

c.15 2-tert-Butyl-4-{4-[3-(4-methyl-5-ethyl-4H-[1,2,4]triazol-3-ylsulfanyl)-propyl]-piperazin-1-yl}-6-trifluoromethyl-pyrimidine hydrochloride 1.5 g of 4-methyl-5-ethyl-4H-[1,2,4]triazole-3-thiol (10.75 mmol) were reacted with 3.92 g of 2-tert-butyl-4-[4-(3-chloro-propyl)-piperazin-1-yl]-6-trifluoromethyl-pyrimidine (10.75 mmol) to yield 3.0 g of the title compound.

MS (ESI) m/z: 472.2 [M+H]$^+$ $^1$H-NMR (DMSO): δ [ppm] 11.9 (s, 1H, broad), 7.25 (s, 1H), 4.4-5.0 (m, 2H, broad), 3.25-3.75 (m, broad, 4H), 3.6 (s, 3H), 3.4 (m, 2H), 3.2 (m, 2H), 3.1 (m, 2H), 2.95 (m, 2H), 2.2 (m, 2H), 1.2-1.4 (m, 12H), c.16 2-tert-Butyl-4-{4-[3-(4-methyl-5-methoxymethyl-4H-[1,2,4]triazol-3-ylsulfanyl)-propyl]-piperazin-1-yl}-6-trifluoromethyl-pyrimidine hydrochloride 1.5 g of 4-methyl-5-methoxymethyl-4H-[1,2,4]triazole-3-thiol (9.42 mmol) were reacted with 3.44 g 2-tert-Butyl-4-[4-(3-chloro-propyl)-piperazin-1-yl]-6-trifluoromethyl-pyrimidine (9.42 mmol) to yield 3.1 g of the title compound.

MS (ESI) m/z: 488.3 [M+H]$^+$

¹H-NMR (DMSO): δ [ppm] 14.4 (s, 1H, broad), 12.1 (s, 1H, broad), 7.9 (s, broad, 2H), 7.2 (s, 1H), 5.0 (m, 1H, broad), 4.7 (s, 3H), 4.5 (m, 1H, broad), 3.85 (m, 1H), 3.9-3.5 (m, 3H), 3.65 (s, 3H), 3.1-3.45 (m, 6H), 2.95 (m, 2H), 2.2 (m, 2H), 1.7 (m, 2H), 1.45 (s, 9H), 0.95 (m, 3H)

c.17 2-tert-Butyl-4-{4-[3-(4-methyl-5-cyclopropyl-4H-[1,2,4]triazol-3-ylsulfanyl)-propyl]-piperazin-1-yl}-6-trifluoromethyl-pyrimidine hydrochloride 0.53 g of 4-methyl-5-methyl-4H-[1,2,4]triazole-3-thiol (3 mmol) were reacted with 1.09 g of 2-tert-butyl-4-[4-(3-chloro-propyl)-piperazin-1-yl]-6-trifluoromethyl-pyrimidine to yield 0.77 g of the title compound as a solid.
Melting point: 182-184° C.
¹H-NMR (CDCl₃): δ [ppm] 6.6 (s, 1H), 3.75 (m, 4H, broad), 3.6 (s, 3H), 3.2 (m, 2H), 2.6 (m, broad, 6H), 2.0 (m, broad, 2H), 1.75 (m, 1H), 1.3 (s, 9H), 1.1 (m, 2H), 1.05 (m, 2H)

c.18 2-tert-Butyl-4-{4-[3-(4-methyl-5-cyclobutyl-4H-[1,2,4]triazol-3-ylsulfanyl)-propyl]-piperazin-1-yl}-6-trifluoromethyl-pyrimidine acetate 1 g of 2-tert-butyl-4-[4-(3-chloro-propyl)-piperazin-1-yl]-6-trifluoromethyl-pyrimidine (2.74 mmol) were reacted with 0.46 g of 4-methyl-5-cyclobutyl-4H-[1,2,4]triazole-3-thiol (2.74 mmol) to yield after lyophilisation 0.12 g of the product.
MS (ESI) m/z: 498.2 [M+H]⁺
¹H-NMR (DMSO): δ [ppm] 7.05 (s, 1H), 3.75 (m, broad, 4H), 3.4 (s, 3H), 3.1 (m, 2H), 3.15 (m, 2H), 2.45 (m, 6H), 2.35 (m, 4H), 2.05 (m, 1H), 1.85 (m, 2H), 1.75 (m, 2H), 1.3 (s, 9H).

c.19 2-tert-Butyl-4-{4-[3-(4-methyl-5-cyclopropyl-4H-[1,2,4]triazol-3-ylsulfanyl)-propyl]-piperazin-1-yl}-6-ethyl-pyrimidine hydrochloride 1 g of 4-methyl-5-cyclopropyl-4H-[1,2,4]triazole-3-thiol (6.44 mmol) were reacted with 2.09 g of 2-tert-butyl-4-[4-(3-chloro-propyl)-piperazin-1-yl]-6-ethyl-pyrimidine (6.44 mmol) to yield 1.2 g of the title compound.
MS (ESI) m/z: 444.4 [M+H]⁺
¹H-NMR (DMSO):): δ [ppm] 14.35 (s, 1H, broad), 12.1 (s, 1H, broad) 7.15 (s, 1H), 5.0 (m, 1H, very broad), 4.5 (m, 1H, very broad), 3.05-4.0 (several m, very broad, 6H), 3.75 (s, 3H), 3.4 (m, 2H), 3.25 (m, 2H), 3.0 (m, 2H), 2.3 (m, 1H), 2.2 (m, 2H), 1.45 (s, 9H), 1.2-1.35 (m, 7H)

c.20 2-tert-Butyl-4-{4-[3-(4-methyl-5-cyclobutyl-4H-[1,2,4]triazol-3-ylsulfanyl)-propyl]-piperazin-1-yl}-6-difluoromethyl-pyrimidine hydrochloride 0.488 g of 4-methyl-5-cyclobutyl-4H-[1,2,4]triazole-3-thiol (2.88 mmol) were reacted with 1 g of 2-tert-butyl-4-[4-(3-chloro-propyl)-piperazin-1-yl]-6-difluoromethyl-pyrimidine (2.88 mmol) to yield 0.44 g of the product as a white solid after drying.
MS (ESI) m/z: 480.4 [M+H]⁺
¹H-NMR (DMSO): δ [ppm] 11.8 (s, broad, 1H), 7.05 (s, 1H), 6.75 (t, 1H, CHF2), 4.6 (m, broad, 2H), 3.85 (m, 1H), 3.55 (m, broad, 4H), 3.5 (s, 3H), 3.4 (m, 2H), 3.2 (m, 2H), 3.1 (m, 2H), 2.35-2.55 (m, 4H), 2.2 (m, 2H), 2.1 (m, 1H), 1.9 (m, 1H), 1.3 (s, 9H)

c.21 2-tert-Butyl-4-{4-[3-(4-methyl-5-cyclopropyl-4H-[1,2,4]triazol-3-ylsulfanyl)-propyl]-piperazin-1-yl}-6-difluoromethyl-pyrimidine hydrochloride 0.67 g of 4-methyl-5-cyclopropyl-4H-[1,2,4]triazole-3-thiol (4.32 mmol) were reacted with 1.5 g of 2-tert-butyl-4-[4-(3-chloro-propyl)-piperazin-1-yl]-6-difluoromethyl-pyrimidine (4.32 mmol) to yield 0.45 g of the title compound.
MS (ESI) m/z: 466.4 [M+H]⁺
¹H-NMR (DMSO): δ [ppm] 11.95 (s, 1H, broad), 9.8 (s, 3H, broad), 7.0 (s, 1H), 6.8 (t, 1H, CHF2), 4.7 (s, 2H), 4.6 (m, 2H, broad), 3.45-3.7 (m, 3H, broad), 3.6 (s, 3H), 3.4 (m, 2H), 3.35 (s, 3H), 3.2 (m, 2H), 2.95-3.2 (m, 2H, broad), 2.2 (m, 2H), 2.0 (s, 1H), 1.3 (s, 9H), 1.2 (m, 1H)

c.22 2-tert-Butyl-4-{4-[3-(4-methyl-4H-[1,2,4]triazol-3-ylsulfanyl)-propyl]-piperazin-1-yl}-6-propyl-pyrimidine fumarate Reaction of 1 g of 2-tert-butyl-4-[4-(3-chloro-propyl)-piperazin-1-yl]-6-propyl-pyrimidine (2.95 mmol) with 0.37 g of 4-methyl-4H-[1,2,4]triazole-3-thiol (3.21 mmol) yielded 0.33 g (21%) of the title compound as a solid.
MS (ESI) m/z: 418.1 [M+H]⁺
¹H-NMR (DMSO): δ [ppm] 8.6 (s, 1H), 6.65 (s, 2H, fumarate), 6.45 (s, 1H), 3.65 (m, 4H), 3.6 (s, 3H), 3.15 (m, 2H), 2.6 (m, 6H), 2.45 (m, 2H), 1.9 (m, 2H), 1.65 (m, 2H), 1.25 (s, 9H), 0.9 (m, 3H)

c.23 2-tert-Butyl-4-{4-[3-(4-methyl-4H-[1,2,4]triazol-3-ylsulfanyl)-propyl]-piperazin-1-yl}-6-trifluoromethyl-pyrimidine hydrochloride 1 g of 4-methyl-4H-[1,2,4]triazole-3-thiol (8.7 mmol) were reacted with 3.2 g of 2-tert-butyl-4-[4-(3-chloro-propyl)-piperazin-1-yl]-6-trifluoromethyl-pyrimidine (8.7 mmol to yield 2.1 g of the title compound as a solid.
Melting point: 92-95° C.
MS (ESI) m/z: 444 [M+H]⁺
¹H-NMR (CDCl₃): δ [ppm] 8.15 (s, 1H), 6.6 (s, 1H), 3.75 (m, broad, 4), 3.6 (s, 3H), 2.55 (m, 6H), 2.0 (m, 2H), 1.35 (s, 9H)

c.24 2-tert-Butyl-4-{4-[3-(4-methyl-4H-[1,2,4]triazol-3-ylsulfanyl)-propyl]piperazin-1-yl}-6-difluoromethyl-pyrimidine hydrochloride 0.33 g of 4-methyl-4H-[1,2,4]triazole-3-thiol (2.88 mmol) were reacted with 1 g of 2-tert-Butyl-4-[4-(3-chloro-propyl)-piperazin-1-yl]-6-difluoromethyl-pyrimidine (2.88 mmol) to yield 0.444 g of the product as a white solid.
MS (ESI) m/z: 426.4 [M+H]⁺
¹H-NMR (DMSO): δ [ppm] 11.9 (s, broad, 1H), 9.6 (s, 1H), 7.65 (s, broad, 4H), 7.05 (s, 1H), 6.8 (t, 1H, CHF2), 4.65 (m, broad, 2H), 3.75 (s, 3H), 3.6 (m, broad, 4H), 3.4 (m, 2H), 3.25 (m, 2H), 3.1 (m, 2H), 2.2 (m, 2H), 1.3 (s, 9H).

c.25 2-tert-Butyl-4-{4-[3-(4-methyl-5-trifluoromethyl-4H-[1,2,4]triazol-3-ylsulfanyl)-propyl]-piperazin-1-yl}-6-propyl-pyrimidine hydrochloride Reaction of 1 g of 2-tert-butyl-4-[4-(3-chloro-propyl)-piperazin-1-yl]-6-propyl-pyrimidine (2.95 mmol) with 0.6 g 4-Methyl-5-trifluoromethyl-4H-[1,2,4]triazole-3-thiol (3.28 mmol), yielded 0.3 g (18%) of the title compound as crystalline hydrochloride salt.
MS (ESI) m/z: 486.2 [M+H]⁺
¹H-NMR (DMSO): δ [ppm] 14.3 (s, 1H, broad), 12.1 (s, 1H, broad), 7.15 (s, 1H), 5.0 (m, 1H), 4.5 (m, 1H), 3.85 (m, 1H), 3.5-3.8 (m, 3H), 3.7 (s, 3H), 3.4 (m, 2H), 3.2 (m, 4H), 2.9 (m, 2H), 2.2 (m, 2H), 1.7 (m, 2H), 1.45 (s, 9H), 0.95 (m, 3H)

c.26 2-tert-Butyl-4-{4-[3-(4-methyl-5-isopropyl-4H-[1,2,4]triazol-3-ylsulfanyl)-propyl]-piperazin-1-yl}-6-trifluoromethyl-pyrimidine hydrochloride 0.5 g of 4-methyl-5-isopropyl-4H-[1,2,4]triazole-3-thiol (3.18 mmol) were reacted with 1.16 g of 2-tert-butyl-4-[4-(3-chloro-propyl)-piperazin-1-yl]-6-trifluoromethyl-pyrimidine (3.18 mmol) to yield 1.1 g of the title compound.

MS (ESI) m/z: 486.2 [M+H]$^+$ $^1$H-NMR (DMSO): δ [ppm] 11.6 (s, 1H, broad), 7.2 (s, 1H), 4.1 (m, 2H, broad), 3.7 (s, 3H), 3.6 (m, 4H, broad), 3.35-3.45 (m, 3H), 3.25 (m, 2H), 3.1 (m, 2H), 2.2 (m, 2H), 1.4 (d, 6H), 1.3 (s, 9H)

c.27 2-tert-Butyl-4-{4-[3-(4-methyl-5-tert-butyl-4H-[1,2,4]triazol-3-ylsulfanyl)-propyl]-piperazin-1-yl}-6-trifluoromethyl-pyrimidine 0.5 g of 4-methyl-5-tert-butyl-4H-[1,2,4]triazole-3-thiol (2.92 mmol) were reacted with 1.07 g of 2-tert-butyl-4-[4-(3-chloro-propyl)-piperazin-1-yl]-6-trifluoromethyl-pyrimidine (2.92 mmol) to yield 1.05 g of the title compound.

MS (ESI) m/z: 500.3 [M+H]$^+$ c.28 2-tert-Butyl-4-{4-[3-(4-methyl-5-trifluoromethyl-4H-[1,2,4]triazol-3-ylsulfanyl)-propyl]-piperazin-1-yl}-6-ethyl-pyrimidine hydrochloride 0.36 g of 4-methyl-5-trifluoromethyl-4H-[1,2,4]triazole-3-thiol (1.96 mmol) were reacted with 0.64 g 2-tert-butyl-4-[4-(3-chloro-propyl)-piperazin-1-yl]-6-ethyl-pyrimidine (1.96 mmol) to yield 500 mg of the title compound.

MS (ESI) m/z: 472.2 [M+H]$^+$ $^1$H-NMR (DMSO): δ [ppm] 14.1 (s, broad, 1H), 11.95 (s, broad, 1H), 7.0 (s, 1H), 4.9 (m, broad, 1H), 4.45 (m, broad, 1H), 3.75 (m, broad, 1H), 3.65 (s, 3H), 3.6 (m, broad, 3H), 3.4 (m, 3H), 3.3 (m, 2H), 3.15 (m, broad, 2H), 2.85 (m, 2H), 2.15 (m, 2H), 1.35 (s, 9H), 1.3 (m, 3H), c.29 2-tert-Butyl-4-{4-[3-(4-methyl-5-ethyl-4H-[1,2,4]triazol-3-ylsulfanyl)-propyl]-piperazin-1-yl}-6-difluoromethyl-pyrimidine hydrochloride 0.619 g of 4-methyl-5-ethyl-4H-[1,2,4]triazole-3-thiol (4.32 mmol were reacted with 1.5 g of 2-tert-Butyl-4-[4-(3-chloro-propyl)-piperazin-1-yl]-6-difluoromethyl-pyrimidine (4.32 mmol), to yield 0.5 g of the title compound.

MS (ESI) m/z: 454.2 [M+H]$^+$ $^1$H-NMR (DMSO): δ [ppm] 11.95 (s, 1H, broad), 10.2 (s, 1H, broad), 7.1 (s, 1H), 6.8 (t, 1H, CHF2), 4.65 (s, 2H), 3.65 (s, 3H), 3.5-3.7 (m, 4H, broad), 3.45 (m, 2H), 3.2 (m, 2H), 2.95-3.2 (m, 4H, broad), 2.2 (m, 2H), 1.25-1.4 (m, 12H)

The compounds II of examples c.30 to c.38 can be obtained by analogy to the methods described in the examples c.1 or c.2:

c.30 2-tert-Butyl-4-{4-[3-(4-methyl-5-methyl-4H-[1,2,4]triazol-3-ylsulfanyl)-propyl]-piperazin-1-yl}-6-(1-methylcycloproyl)-pyrimidine hydrochloride c.31 2-tert-Butyl-4-{4-[3-(4-methyl-5-(4-fluorophenyl)-4H-[1,2,4]triazol-3-ylsulfanyl)-propyl]-piperazin-1-yl}-6-trifluoromethyl-pyrimidine hydrochloride c.32 2-tert-Butyl-4-{4-[3-(4-methyl-5-phenyl-4H-[1,2,4]triazol-3-ylsulfanyl)-propyl]-piperazin-1-yl}-6-trifluoromethyl-pyrimidine hydrochloride c.33 2-tert-Butyl-4-{4-[3-(4-methyl-5-(1-methylpyrrol-2-yl)-4H-[1,2,4]triazol-3-ylsulfanyl)-propyl]-piperazin-1-yl}-6-trifluoromethyl-pyrimidine hydrochloride c.34 2-tert-Butyl-4-{4-[3-(4-methyl-5-cyclobutyl-4H-[1,2,4]triazol-3-ylsulfanyl)-propyl]-piperazin-1-yl}-6-tert-butyl-pyrimidine hydrochloride c.35 2-tert-Butyl-4-{4-[3-(4-methyl-5-phenyl-4H-[1,2,4]triazol-3-ylsulfanyl)-propyl]-piperazin-1-yl}-6-tert-butyl-pyrimidine hydrochloride c.36 2-tert-Butyl-4-{4-[3-(4-methyl-5-methoxymethyl-4H-[1,2,4]triazol-3-ylsulfanyl)-propyl]-piperazin-1-yl}-6-tert-butyl-pyrimidine hydrochloride c.37 2-tert-Butyl-4-{4-[3-(4-methyl-5-(1-methylpyrrol-2-yl)-4H-[1,2,4]triazol-3-ylsulfanyl)-propyl]-piperazin-1-yl}-6-tert-butyl-pyrimidine hydrochloride c.38 2-tert-Butyl-4-{4-[3-(4-methyl-4H-[1,2,4]triazol-3-ylsulfanyl)-propyl]-piperazin-1-yl}-6-isopropyl-pyrimidine hydrochloride c-39 2-tert-Butyl-4-{4-[3-(1-methyl-1H-[1,2,4]triazole-3-sulfanyl)-propyl]-piperazin-1-yl}-6-trifluoromethyl-pyrimidine hydrochloride

ESI-MS: 444.25 [M+H]$^+$ $^1$H-NMR (DMSO): δ [ppm] 11.7 (s, broad, 1H), 8.5 (s, 1H), 7.2 (s, 1H), 3.8 (s, 3H), 3.45-3.7 (m, 4H), 3.1-3.2 (m, 4H), 3.0-3.1 (m, 2H), 2.1-2.2 (m, 2H), 1.3 (s, 9H), 1.05 (m, 2H).

c-40 2,6-di-tert-Butyl-4-{4-[3-(2-methyl-1H-[1,2,4]triazole-3-sulfanyl)-propyl]-piperazin-1-yl}-pyrimidine hydrochloride

ESI-MS: 432.25 [M+H]$^+$ $^1$H-NMR (DMSO): δ [ppm] 12.5 (s, broad, 1H), 12.15 (s, broad, 1H), 8.0 (s, 1H), 6.9 (s, 1H), 5.0 (m, broad, 1H), 4.7 (m, broad, 1H), 3.75 (s, 3H), 3.6-3.9 (several m, broad, 4H), 3.3 (m, 2H), 3.1-3.3 (m, 4H), 2.2 (m, 2H), 1.4-1.5 (m, 18H).

c-41 2,6-di-tert-Butyl-4-{4-[3-(1H-[1,2,4]triazole-3-sulfanyl)-propyl]-piperazin-1-yl}-pyrimidine

ESI-MS: 418.2 [M+H]$^+$ $^1$H-NMR (CDCl$_3$): δ [ppm] 7.9 (s, 1H), 6.3 (s, 1H), 3.8 (m, 4H), 3.2 (m, 4H), 2.6-2.7 (m, 6H), 2.0-2.1 (m, 2H), 1.3 (s, 9H), 1.25 (s, 9H).

c-42 2-tert-Butyl-4-{4-[3-(4-methyl-1H-[1,2,4]triazole-3-sulfanyl)-propyl]-piperazin-1-yl}-6-cyclopentyl-pyrimidine

ESI-MS: 444.25 [M+H]$^+$ $^1$H-NMR (CDCl$_3$): δ [ppm] 8.1 (s, 1H), 6.15 (s, 1H), 3.65 (m, 4H), 3.6 (s, 3H), 3.3-3.4 (m, 2H), 2.9-3.0 (m, 1H), 2.45-2.6 (m, 6H), 1.9-2.1 (m, 4H), 1.7-1.85 (m, 4H), 1.6-1.7 (m, 2H), 1.3 (s, 9H).

c-43 2,6-di-tert-Butyl-4-{4-[3-(1-methyl-1H-[1,2,4]
triazole-3-sulfanyl)-propyl]-piperazin-1-yl}-pyrimi-
dine ESI-MS: 432.25 [M+H]$^+$
$^1$H-NMR (CDCl$_3$): δ [ppm] 7.95 (s, 1H), 6.23 (s, 1H), 3.85
(s, 3H), 3.6-3.7 (m, 4H), 3.1-3.2 (m, 2H), 2.5 (m, 6H), 1.95
(m, 2H), 1.3 (s, 9H), 1.25 (s, 9H).

c-44 2-tert-Butyl-4-{4-[3-(1-methyl-1H-[1,2,4]triaz-
ole-3-sulfanyl)-propyl]-piperazin-1-yl}-6-propyl-
pyrimidine

ESI-MS: 418.5 [M+H]$^+$

II. Preparation of the Compounds I

Example 1

2,4-Di-tert-butyl-6-{4-[3-(4,5-dimethyl-4H-[1,2,4]
triazole-3-sulfinyl)-propyl]-piperazin-1-yl}-pyrimi-
dine 10 g of 2,4-di-tert-butyl-6-{4-[3-(4,5-dimethyl-4H-[1,2,4]
triazol-3-ylsulfanyl)-propyl]-piperazin-1-yl}-pyrimidin
(18.01 mmol) were dissolved in 300 ml water. At room tem-
perature, 9 ml of 2 N aqueous hydrochlorid acid (18.01 mmol)
were added. The solution was cooled to 5° C. and 5.54 g (9.0
mmol) of oxone added in portions. After consumption of the
starting material, the crude reaction product was isolated and
subjected to a silica gel chromatography with ethyl acetate,
ethyl acetate-methanol 15:1 to 8:1. Isolated were 1.16 g of
2,4-di-tert-butyl-6-{4-[3-(4,5-dimethyl-4H-[1,2,4]triazole-
3-sulfonyl)-propyl]-piperazin-1-yl}-pyrimidine (Example 4)
and 6.5 g of 2,4-di-tert-butyl-6-{4-[3-(4,5-dimethyl-4H-[1,2,
4]triazole-3-sulfinyl)-propyl]-piperazin-1-yl}-pyrimidine.
The latter product was dissolved in 10 ml of n-hexane and
crystallized overnight in the refrigerator to yield 5.6 g of the
desired product.
ESI-MS: 462.3 [M+H]$^+$
$^1$H-NMR (CDCl$_3$): δ [ppm] 6.25 (s, 1H), 3.85 (s, 3H),
3.5-3.7 (m, 6H), 2.45-2.65 (m, 9H), 2.0-2.2 (m, 2H), 1.35 (s,
9H), 1.3 (s, 9H).

Example 2

2-tert-Butyl-4-cyclobutyl-6-{4-[3-(4-methyl-4H-[1,
2,4]triazole-3-sulfonyl)-propyl]-piperazin-1-yl}-
pyrimidine 38 mg were obtained as described for example 1.
ESI-MS: 462.3 [M+H]$^+$
$^1$H-NMR (CDCl$_3$): δ [ppm] 8.2 (s, 1H), 6.1 (s, 1H), 4.0 (s,
3H), 3.8 (m, 2H), 3.6-3.7 (m, 4H), 3.4 (m, 1H), 2.45-2.6 (m,
6H), 2.1-2.35 (m, 6H), 2.0 (m, 1H), 1.9 (m, 1H), 1.35 (s, 9H).

Example 3

2-tert-Butyl-4-cyclobutyl-6-{4-[3-(4-methyl-4H-[1,
2,4]triazole-3-sulfinyl)-propyl]-piperazin-1-yl}-pyri-
midine 550 mg were obtained as described for example 1.
ESI-MS: 446.3 [M+H]$^+$
$^1$H-NMR (CDCl$_3$): δ [ppm] 8.25 (s, 1H), 6.1 (s, 1H), 4.0 (s,
3H), 3.5-3.7 (m, 6H), 3.4 (m, 1H), 2.45-2.6 (m, 6H), 2.25 (m,
4H), 2.15 (m, 1H), 1.95-2.1 (m, 2H), 1.9 (m, 1H), 1.35 (s, 9H).

Example 4

2,4-Di-tert-butyl-6-{4-[3-(4,5-dimethyl-4H-[1,2,4]
triazole-3-sulfonyl)-propyl]-piperazin-1-yl}-pyrimi-
dine 1.16 g were obtained from the silica gel chromatography of
Example 1.
ESI-MS: 478.3 [M+H]$^+$
$^1$H-NMR (CDCl$_3$): δ [ppm] 6.25 (s, 1H), 3.85 (s, 3H), 3.8
(m, 2H), 3.65 (m, 4H), 2.45-2.65 (m, 9H), 2.1-2.2 (m, 2H),
1.2-1.4 (18H).

Example 5

2-tert-Butyl-4-{4-[3-(5-ethyl-4-methyl-4H-[1,2,4]
triazole-3-sulfinyl)-propyl]-piperazin-1-yl}-6-pro-
pyl-pyrimidine hydrochloride 200 mg were obtained as described for example 1. The
hydrochloride salt was formed by addition of HCl/diethyl
ether and careful evaporation of the solvent.
ESI-MS: 462.5 [M+H]$^+$
$^1$H-NMR (d$_6$-DMSO): δ [ppm] 14.3 (s, broad, 1H), 12.1 (s,
broad, 1H), 7.15 (s, 1H), 5.05 (m, broad, 1H), 4.5 (m, broad,
1H), 3.85 (m, broad, 1H), 3.85 (s, 3H), 3.5-3.75 (m, 5H), 3.3
(m, 2H), 3.2 (m, 2H), 2.95 (m, 2H), 2.85 (m, 2H), 2.25 (m,
2H), 1.7 (m, 2H), 1.45 (9H), 1.3 (t, 3H), 0.95 (t, 3H).

Example 6

2-tert-Butyl-4-{4-[3-(4,5-dimethyl-4H-[1,2,4]triaz-
ole-3-sulfinyl)-propyl]-piperazin-1-yl}-6-(1-methyl-
cyclopropyl)-pyrimidine 144 mg were obtained as described for example 1.
ESI-MS: 460.4 [M+H]$^+$
$^1$H-NMR (CDCl$_3$): δ [ppm] 6.3 (s, 1H), 3.85 (s, 3H), 3.5-
3.7 (m, 6H), 2.45-2.65 (m, 9H), 2.0-2.2 (m, 2H), 1.4 (s, 3H),
1.35 (m, 2H), 1.3 (s, 9H), 0.7 (m, 2H).

Example 7

2-tert-Butyl-4-{4-[3-(4,5-dimethyl-4H-[1,2,4]triaz-
ole-3-sulfinyl)-propyl]-piperazin-1-yl}-6-trifluorom-
ethyl-pyrimidine hydrochloride 360 mg were obtained as described for example 1. The
hydrochloride salt was formed by addition of HCl/diethyl
ether and careful evaporation of the solvent.
ESI-MS: 474.1 [M+H]$^+$
$^1$H-NMR (DMSO): δ [ppm] 11.8 (s, very broad, 1H), 7.2
(s, 1H), 4.7 (m, very broad, 2H), 3.8 (s, 3H), 3.45-3.7 (m,
broad, 6H), 3.25 (m, broad, 2H), 3.1 (m, broad, 2H), 2.5 (s,
3H), 2.25 (m, 2H), 1.3 (s, 9H).

Example 8

2-tert-Butyl-4-{4-[3-(4,5-dimethyl-4H-[1,2,4]triaz-
ole-3-sulfinyl)-propyl]-piperazin-1-yl}-6-propyl-
pyrimidine hydrochloride 100 mg were obtained as described for example 1. The
hydrochloride salt was formed by addition of HCl/diethyl
ether and careful evaporation of the solvent.
ESI-MS: 448.5 [M+H]$^+$ ¹H-NMR (DMSO): δ [ppm] 14.15 (s, very broad, 1H), 12.05 (s, very broad, 1H), 7.15 (s, 1H), 5.0 (m, broad, 1H), 4.2-4.7 (m, broad, 1H), 3.85 (m, broad, 1H), 3.8 (s, 3H), 3.45-3.75 (m, broad, 5H), 3.3 (m, broad, 2H), 3.2 (m, broad, 2H), 2.9 (m, broad, 2H), 2.5 (s, 3H), 2.25 (m, 2H), 1.7 (m, 2H), 1.4 (s, 9H), 0.95 (t, 3H).

Example 9

2-Di-tert-butyl-6-{4-[3-(4,5-dimethyl-4H-[1,2,4]triazole-3-sulfonyl)-propyl]-piperazin-1-yl}-6-propyl-pyrimidine 30 mg were obtained as described for example 1.

Example 10

2-tert-Butyl-4-{4-[3-(4,5-dimethyl-4H-[1,2,4]triazole-3-sulfonyl)-propyl]-piperazin-1-yl}-6-(1-methylcyclopropyl)-pyrimidine 24 mg were obtained as described for example 1.
ESI-MS: 476.1 [M+H]$^+$

Example 11

2-tert-Butyl-4-{4-[3-(4,5-dimethyl-4H-[1,2,4]triazole-3-sulfonyl)-propyl]-piperazin-1-yl}-6-trifluoromethyl-pyrimidine 21.9 mg were obtained as described for example 1.
ESI-MS: 490.1 [M+H]$^+$

Example 12

2-tert-Butyl-4-{4-[3-(5-ethyl-4-methyl-4H-[1,2,4]triazole-3-sulfonyl)-propyl]-piperazin-1-yl}-6-propyl-pyrimidine 19.3 mg were obtained as described for example 1.
ESI-MS: 478.5 [M+H]$^+$

Example 13

Enantiomer #1 of 2,4-Di-tert-butyl-6-{4-[3-(4,5-dimethyl-4H-[1,2,4]triazole-3-sulfinyl)-propyl]-piperazin-1-yl}-pyrimidine Chiral separation of 100 mg racemic of 2,4-di-tert-butyl-6-{4-[3-(4,5-dimethyl-4H-[1,2,4]triazole-3-sulfinyl)-propyl]-piperazin-1-yl}-pyrimidine (example 1) (0.5 μg/ml) was performed on a Chiracel OD column using as eluent a mixture containing n-hexane/ethanol/trifluoroacetic acid (8:2:0.01) to yield 16 mg of enantiomer-1 and 28 mg of enantiomer-2 (example 14).

Example 14

Enantiomer #2 of 2,4-di-tert-butyl-6-{4-[3-(4,5-dimethyl-4H-[1,2,4]triazole-3-sulfinyl)-propyl]-piperazin-1-yl}-pyrimidine 28 mg enantiomer-2 was obtained from the chiral separation of 2,4-di-tert-butyl-6-{-4-[3-(4,5-dimethyl-4H-[1,2,4]triazole-3-sulfinyl)-propyl]-piperazin-1-yl}-pyrimidine (example 1) as described above.

Example 15

2-tert-Butyl-4-(4-{3-[5-(4-fluoro-phenyl)-4-methyl-4H[1,2,4]triazole-3-sulfinyl]-propyl}-piperazin-1-yl)-6-trifluoromethyl-pyrimidine 1.3 g were obtained as described for example 1.
ESI-MS: 554.2 [M+H]$^+$
¹H-NMR (CDCl₃): δ [ppm] 7.65 (m, 2H), 7.25 (m, 2H), 6.6 (s, 1H), 3.95 (s, 3H), 3.7 (m, 6H), 2.6 (m, 2H), 2.55 (m, 4H), 2.05-2.25 (m, 2H), 1.3 (s, 9H).

Example 16

2-tert-Butyl-4-(4-{3-[5-(4-fluoro-phenyl)-4-methyl-4H-[1,2,4]triazole-3-sulfonyl]-propyl}-piperazin-1-yl)-6-trifluoromethyl-pyrimidine hydrochloride 166 mg were obtained as described for example 1. The hydrochloride salt was formed by addition of HCl/diethyl ether and careful evaporation of the solvent.
ESI-MS: 570.2 [M+H]$^+$
¹H-NMR (DMSO): δ [ppm] 11.5 (s, very broad, 1H), 7.85 (m, 2H), 7.45 (m, 2H), 7.2 (s, 1H), 4.65 (m, very broad, 2H), 3.9 (m, 2H), 3.85 (s, 3H), 3.5-3.6 (m, broad, 4H), 3.25 (m, broad, 2H), 3.1 (m, broad, 2H), 2.3 (m, 2H), 1.3 (s, 9H).

Example 17

2,4-Di-tert-butyl-6-{4-[3-(4-methyl-4H-[1,2,4]triazole-3-sulfonyl)-propyl]-piperazin-1-yl}-pyrimidine The title compound was obtained as described for example 1
ESI-MS: 464.2 [M+H]$^+$
¹H-NMR (CDCl₃): δ [ppm] 8.2 (s, 1H), 6.25 (s, 1H), 4.0 (s, 3H), 3.8 (m, 2H), 3.65 (m, 4H), 2.5-2.6 (several m, 6H), 2.1-2.2 (m, 2H), 1.35 (s, 9H), 1.3 (s, 9H).

Example 18

2,4-Di-tert-butyl-6-{4-[3-(4-methyl-4H-[1,2,4]triazole-3-sulfinyl)-propyl]-piperazin-1-yl}-pyrimidine The title compound was obtained as described for example 1
ESI-MS: 448.2 [M+H]$^+$
¹H-NMR (CDCl₃): δ [ppm] 8.2 (s, 1H), 6.25 (s, 1H), 4.0 (s, 3H), 3.55-3.7 (m, 6H), 2.6 (m, 2H), 2.5 (m, 4H), 2.15 (m, 1H), 2.05 (m, 1H), 1.3 (s, 9H), 1.25 (s, 9H).

Example 19

2-tert-Butyl-4-{4-[3-(1-methyl-1H-[1,2,4]triazole-3-sulfonyl)-propyl]-piperazin-1-yl}-6-trifluoromethyl-pyrimidine hydrochloride 1-Methyl-1H-[1,2,4]triazole-3-thiol was purchased from Prosyntest, Estonia.
The title compound was obtained as described for example 1
ESI-MS: 476.1 [M+H]$^+$ ¹H-NMR (d₆-DMSO): δ [ppm] 11.65 (s, broad, 1H), 8.85 (s, 1H), 7.2 (s, 1H), 4.35-4.85 (several m, broad, 3H), 4.0 (s, 3H), 3.6 (m, 2H), 3.5-3.6 (m, 3H), 3.25 (m, 2H), 3.0-3.15 (m, 2H), 2.2 (m, 2H), 1.3 (s, 9H).

Example 20

2,4-Di-tert-butyl-6-{4-[3-(2-methyl-2H-[1,2,4]triazole-3-sulfonyl)-propyl]-piperazin-1-yl}-pyrimidine hydrochloride 2-Methyl-1H-[1,2,4]triazole-3-thiol was purchased.
The title compound was obtained as described for example 1

ESI-MS: 464.2 [M+H]$^+$
¹H-NMR (d₆-DMSO): δ [ppm] 12.1 (s, broad, 1H), 8.3 (s, 1H), 6.8 (s, broad, 1H), 4.25-5.1 (several m, broad, 4H), 4.2 (s, 3H), 3.9 (m, 2H), 3.45-3.8 (several m, 2H), 3.25 (m, 2H), 3.15 (m, broad, 2H), 2.2-2.3 (m, 2H), 1.4 (s, broad, 18H).

Example 21

2-tert-Butyl-4-{4-[3-(1-methyl-1H-[1,2,4]triazole-3-sulfinyl)-propyl]-piperazin-1-yl}-6-trifluoromethyl-pyrimidine hydrochloride 1-Methyl-1H-[1,2,4]triazole-3-thiol was purchased from Prosyntest, Estonia.
The title compound was obtained as described for example 1

ESI-MS: 460.1 [M+H]$^+$
¹H-NMR (d₆-DMSO): δ [ppm] 11.55 (s, broad, 1H), 8.8 (s, 1H), 7.2 (s, 1H), 4.5-5.0 (several m, broad, 2H), 4.0 (s, 3H), 3.4-3.6 (several m, 4H), 3.3 (m, 2H), 3.25 (m, 2H), 3.1 (m, 2H), 2.15 (m, 2H), 1.3 (s, 9H).

Example 22

2,4-Di-tert-butyl-6-{4-[3-(1H-[1,2,4]triazole-3-sulfonyl)-propyl]-piperazin-1-yl}-pyrimidine 1H-[1,2,4]triazole-3-thiol was purchased.
The title compound was obtained as described for example 1

ESI-MS: 450.2 [M+H]$^+$
¹H-NMR (d₆-DMSO): δ [ppm] 8.9 (s, 1H), 6.45 (s, 1H), 3.6 (m, 4H), 3.5 (m, 2H), 2.4 (m, 6H), 1.85 (m, 2H), 1.2-1.35 (2s, 18H).

Example 23

2-tert-Butyl-4-{4-[3-(4-methyl-1H-[1,2,4]triazole-3-sulfonyl)-propyl]-piperazin-1-yl}-6-isopropyl-pyrimidine The title compound was obtained as described for example 1

ESI-MS: 450.2 [M+H]$^+$
¹H-NMR (d₆-DMSO): δ [ppm] 8.85 (s, 1H), 6.4 (s, 1H), 3.9 (s, 3H), 3.7 (m, 2H), 3.6 (m, 4H), 3.3 (s, 3H), 2.75 (m, 1H), 2.4 (m, 4H), 1.9 (m, 2H), 1.3 (s, 9H), 1.2 (d, 6H).

Example 24

2-tert-Butyl-4-{4-[3-(4-methyl-1H-[1,2,4]triazole-3-sulfonyl)-propyl]-piperazin-1-yl}-6-cyclopentyl-pyrimidine The title compound was obtained as described for example 1

ESI-MS: 476.3 [M+H]$^+$
¹H-NMR (CDCl₃): δ [ppm] 8.2 (s, 1H), 6.15 (s, 1H), 4.0 (s, 3H), 3.8 (m, 2H), 3.6 (m, 4H), 2.95 (m, 1H), 2.55 (m, 1H), 2.45-2.6 (m, 5H), 2.2 (m, 2H), 1.95 (m, 2H), 1.8 (m, 4H), 1.65 (m, 2H), 1.3 (s, 9H).

Example 25

2-tert-Butyl-4-{4-[3-(4-methyl-1H-[1,2,4]triazole-3-sulfinyl)-propyl]-piperazin-1-yl}-6-cyclopentyl-pyrimidine The title compound was obtained as described for example 1

ESI-MS: 460.14 [M+H]$^+$
¹H-NMR (CDCl₃): δ [ppm] 8.2 (s, 1H), 6.1 (s, 1H), 4.0 (s, 3H), 3.6 (m, 6H), 2.95 (m, 1H), 2.55 (m, 1H), 2.45-2.6 (m, 5H), 2.15 (m, 1H), 2.05 (m, 1H), 1.95 (m, 2H), 1.8 (m, 4H), 1.65 (m, 2H), 1.3 (s, 9H).

Example 26

2-tert-Butyl-4-{4-[3-(4-methyl-1H-[1,2,4]triazole-3-sulfonyl)-propyl]-piperazin-1-yl}-6-propyl-pyrimidine The title compound was obtained as described for example 1

ESI-MS: 450.2 [M+H]$^+$
¹H-NMR (CDCl₃): δ [ppm] 8.2 (s, 1H), 6.1 (s, 1H), 4.0 (s, 3H), 3.8 (m, 2H), 3.6-3.7 (m, 4H), 2.45-2.6 (m, 8H), 2.15 (m, 2H), 1.7 (m, 2H), 1.35 (s, 9H), 0.95 (t, 3H).

Example 27

2,6-di-tert-Butyl-4-{4-[3-(1-methyl-1H-[1,2,4]triazole-3-sulfonyl)-propyl]-piperazin-1-yl}-pyrimidine 1-Methyl-1H-[1,2,4]triazole-3-thiol was purchased from Prosyntest, Estonia.
The title compound was obtained as described for example 1

ESI-MS: 464.2 [M+H]$^+$
¹H-NMR (CDCl₃): δ [ppm] 8.2 (s, 1H), 6.25 (s, 1H), 4.05 (s, 3H), 3.55-3.65 (m, 4H), 3.4-3.5 (m, 2H), 2.4-2.55 (m, 6H), 2.0-2.1 (m, 2H), 1.3 (s, 9H), 1.25 (s, 9H).

Example 28

2-tert-Butyl-4-{4-[3-(1-methyl-1H-[1,2,4]triazole-3-sulfinyl)-propyl]-piperazin-1-yl}-6-propyl-pyrimidine hydrochloride 1-Methyl-1H-[1,2,4]triazole-3-thiol was purchased from Prosyntest, Estonia.
The title compound was obtained as described for example 1

ESI-MS: 434.2 [M+H]$^+$
¹H-NMR (DMSO): δ [ppm] 14.3 (s, broad, 1H), 12.1 (s, broad, 1H), 8.8 (s, 1H), 7.15 (s, 1H), 5.0 (m, broad, 1H), 4.5 (m, broad, 1H), 4.0 (s, 3H), 3.05-3.9 (several m, broad, 10H), 2.9-3.0 (m, 2H), 2.1-2.2 (m, 2H), 1.7 (m, 2H), 1.45 (s, 9H), 0.9-1.0 (m, 3H).

Example 29

2-tert-Butyl-4-{4-[3-(1-methyl-1H-[1,2,4]triazole-3-sulfinyl)-propyl]-piperazin-1-yl}-6-propyl-pyrimidine The title compound was obtained as described for example 1

ESI-MS: 450.5 [M+H]$^+$

¹H-NMR (CDCl₃): δ [ppm] 8.2 (s, 1H), 6.1 (s, 1H), 4.05 (s, 3H), 3.55-3.65 (m, 4H), 3.4-3.5 (m, 2H), 2.4-2.6 (m, 8H), 2.0-2.1 (m, 2H), 1.7 (m, 2H), 1.3 (s, 9H), 0.9-1.0 (t, 3H).

Example 30

2,6-di-tert-Butyl-4-{4-[3-(1-methyl-1H-[1,2,4]triazole-3-sulfinyl)-propyl]-piperazin-1-yl}-pyrimidine hydrochloride The title compound was obtained as described for example 1

¹H-NMR (DMSO): δ [ppm] 8.8 (s, 1H), 6.75 (s, broad, 1H), 4.65 (m, broad, 2H), 4.0 (s, 3H), 3.5-3.9 (several m, broad, 8H), 3.2-3.35 (m, 4H), 3.0-3.2 (m, 2H), 2.1-2.2 (m, 2H), 1.2-1.5 (broad, 18H).

Example 31

2-tert-butyl-6-{4-[3-(1H-[1,2,4]triazole-3-sulfonyl)-propyl]-piperazin-1-yl}-6-(1-methyl)cyclopropyl-pyrimidine The title compound was obtained as described for example 1

Example 32

(S)-2-tert-Butyl-4-{4-[3-(1-methyl-1H-[1,2,4]triazole-3-sulfinyl)-propyl]-piperazin-1-yl}-6-propyl-pyrimidine The title compound was obtained as described for example 1

ESI-MS: 434.25 [M+H]⁺

Example 33

(R)-2-tert-Butyl-4-{4-[3-(1-methyl-1H-[1,2,4]triazole-3-sulfinyl)-propyl]-piperazin-1-yl}-6-propyl-pyrimidine The title compound was obtained as described for example 1

ESI-MS: 434.25 [M+H]⁺

The compounds of examples 34 to 164 given in tables 1, 2, 3 or 4 were or can be prepared by analogy to the methods described in the previous examples.

TABLE 1

Compounds of the formula I, wherein Ar is Ar-1.

| Example | R¹ | X | R² |
|---|---|---|---|
| 34 | cyclopropyl | SO | trifluoromethyl |
| 35 | cyclopropyl | SO₂ | trifluoromethyl |
| 36 | cyclobutyl | SO | trifluoromethyl |
| 37 | cyclobutyl | SO₂ | trifluoromethyl |
| 38 | phenyl | SO | trifluoromethyl |
| 39 | phenyl | SO₂ | trifluoromethyl |
| 40 | methoxymethyl | SO | trifluoromethyl |
| 41 | methoxymethyl | SO₂ | trifluoromethyl |
| 42 | trifluoromethyl | SO | trifluoromethyl |
| 43 | trifluoromethyl | SO₂ | trifluoromethyl |
| 44 | N-methyl-pyrrol-2-yl | SO | trifluoromethyl |
| 45 | N-methyl-pyrrol-2-yl | SO₂ | trifluoromethyl |
| 46 | cyclopropyl | SO | tert-butyl |
| 47 | cyclopropyl | SO₂ | tert-butyl |
| 48 | cyclobutyl | SO | tert-butyl |
| 49 | cyclobutyl | SO₂ | tert-butyl |
| 50 | phenyl | SO | tert-butyl |
| 51 | phenyl | SO₂ | tert-butyl |

TABLE 1-continued

Compounds of the formula I, wherein Ar is Ar-1.

| Example | R¹ | X | R² |
|---|---|---|---|
| 52 | methoxymethyl | SO | tert-butyl |
| 53 | methoxymethyl | SO₂ | tert-butyl |
| 54 | trifluoromethyl | SO | tert-butyl |
| 55 | trifluoromethyl | SO₂ | tert-butyl |
| 56 | N-methyl-pyrrol-2-yl | SO | tert-butyl |
| 57 | N-methyl-pyrrol-2-yl | SO₂ | tert-butyl |
| 58 | ethyl | SO | trifluoromethyl |
| 59 | ethyl | SO₂ | trifluoromethyl |
| 60 | H | (S)—SO | trifluoromethyl |
| 61 | H | (S)—SO | propyl |
| 62 | H | (S)—SO | isopropyl |
| 63 | H | (S)—SO | difluoromethyl |
| 64 | H | (S)—SO | cyclobutyl |
| 65 | H | (S)—SO | cyclopentyl |
| 66 | H | (R)—SO | trifluoromethyl |
| 67 | H | (R)—SO | propyl |
| 58 | H | (R)—SO | isopropyl |
| 39 | H | (R)—SO | difluoromethyl |
| 70 | H | (R)—SO | cyclobutyl |
| 71 | H | (R)—SO | cyclopentyl |
| 72 | H | SO₂ | trifluoromethyl |
| 73 | H | SO₂ | propyl |
| 74 | H | SO₂ | difluoromethyl |
| 75 | H | SO₂ | cyclobutyl |
| 76 | H | (S)—SO | trifluoromethyl |
| 77 | H | (S)—SO | difluoromethyl |
| 78 | H | (S)—SO | Tert-butyl |
| 79 | H | (S)—SO | propyl |

TABLE 2

Compounds of the formula I, wherein Ar is Ar-2 and R¹ᵃ is H.

| Example | R¹ | X | R² |
|---|---|---|---|
| 80 | H | (S)—SO | cyclobutyl |
| 81 | H | (S)—SO | isopropyl |
| 82 | H | (R)—SO | trifluoromethyl |
| 83 | H | (R)—SO | difluoromethyl |
| 84 | H | (R)—SO | Tert-butyl |
| 85 | H | (R)—SO | propyl |
| 86 | H | (R)—SO | cyclobutyl |
| 87 | H | (R)—SO | isopropyl |
| 88 | methyl | SO₂ | trifluoromethyl |
| 89 | methyl | SO₂ | propyl |
| 90 | methyl | SO₂ | difluoromethyl |
| 91 | methyl | SO₂ | cyclobutyl |
| 92 | methyl | (S)—SO | trifluoromethyl |
| 93 | methyl | (S)—SO | difluoromethyl |
| 94 | methyl | (S)—SO | Tert-butyl |
| 95 | methyl | (S)—SO | propyl |
| 96 | methyl | (S)—SO | cyclobutyl |
| 97 | methyl | (S)—SO | isopropyl |
| 98 | methyl | (R)—SO | trifluoromethyl |
| 99 | methyl | (R)—SO | difluoromethyl |
| 100 | methyl | (R)—SO | Tert-butyl |
| 101 | methyl | (R)—SO | propyl |
| 102 | methyl | (R)—SO | cyclobutyl |
| 103 | methyl | (R)—SO | isopropyl |

TABLE 3

Compounds of the formula I, wherein Ar is Ar-2 and R¹ᵃ is methyl.

| Example | R¹ | X | R² |
|---|---|---|---|
| 104 | H | SO₂ | difluoromethyl |
| 105 | H | SO₂ | cyclobutyl |
| 106 | H | (S)—SO | trifluoromethyl |
| 107 | H | (S)—SO | difluoromethyl |

TABLE 3-continued

Compounds of the formula I, wherein
Ar is Ar-2 and $R^{1a}$ is methyl.

| Example | $R^1$ | X | $R^2$ |
|---|---|---|---|
| 108 | H | (S)—SO | Tert-butyl |
| 109 | H | (S)—SO | propyl |
| 110 | H | (S)—SO | cyclobutyl |
| 111 | H | (S)—SO | isopropyl |
| 112 | H | (R)—SO | trifluoromethyl |
| 113 | H | (R)—SO | difluoromethyl |
| 114 | H | (R)—SO | Tert-butyl |
| 115 | H | (R)—SO | propyl |
| 116 | H | (R)—SO | cyclobutyl |
| 117 | H | (R)—SO | isopropyl |
| 118 | methyl | $SO_2$ | trifluoromethyl |
| 119 | methyl | $SO_2$ | propyl |
| 120 | methyl | $SO_2$ | difluoromethyl |
| 121 | methyl | $SO_2$ | cyclobutyl |
| 122 | methyl | (S)—SO | trifluoromethyl |
| 123 | methyl | (S)—SO | difluoromethyl |
| 124 | methyl | (S)—SO | Tert-butyl |
| 125 | methyl | (S)—SO | propyl |
| 126 | methyl | (S)—SO | cyclobutyl |
| 127 | methyl | (S)—SO | isopropyl |
| 128 | methyl | (R)—SO | trifluoromethyl |
| 129 | methyl | (R)—SO | difluoromethyl |
| 130 | methyl | (R)—SO | Tert-butyl |
| 131 | methyl | (R)—SO | propyl |
| 132 | methyl | (R)—SO | cyclobutyl |
| 133 | methyl | (R)—SO | isopropyl |

TABLE 4

Compounds of the formula I, wherein
Ar is Ar-3 and $R^{1a}$ is methyl.

| Example | $R^1$ | X | $R^2$ |
|---|---|---|---|
| 134 | H | $SO_2$ | difluoromethyl |
| 135 | H | $SO_2$ | trifluoromethyl |
| 136 | H | $SO_2$ | cyclobutyl |
| 137 | H | (S)—SO | trifluoromethyl |
| 138 | H | (S)—SO | difluoromethyl |
| 139 | H | (S)—SO | Tert-butyl |
| 140 | H | (S)—SO | propyl |
| 141 | H | (S)—SO | cyclobutyl |
| 142 | H | (S)—SO | isopropyl |
| 143 | H | (R)—SO | trifluoromethyl |
| 144 | H | (R)—SO | difluoromethyl |
| 145 | H | (R)—SO | Tert-butyl |
| 146 | H | (R)—SO | propyl |
| 147 | H | (R)—SO | cyclobutyl |
| 148 | H | (R)—SO | isopropyl |
| 149 | methyl | $SO_2$ | trifluoromethyl |
| 150 | methyl | $SO_2$ | propyl |
| 151 | methyl | $SO_2$ | difluoromethyl |
| 152 | methyl | $SO_2$ | cyclobutyl |
| 153 | methyl | (S)—SO | trifluoromethyl |
| 154 | methyl | (S)—SO | difluoromethyl |
| 155 | methyl | (S)—SO | Tert-butyl |
| 156 | methyl | (S)—SO | propyl |
| 157 | methyl | (S)—SO | cyclobutyl |
| 158 | methyl | (S)—SO | isopropyl |
| 159 | methyl | (R)—SO | trifluoromethyl |
| 160 | methyl | (R)—SO | difluoromethyl |
| 161 | methyl | (R)—SO | Tert-butyl |
| 162 | methyl | (R)—SO | propyl |
| 163 | methyl | (R)—SO | cyclobutyl |
| 164 | methyl | (R)—SO | isopropyl |

III. Examples of Galenic Administration Forms

A) Tablets

Tablets of the following composition are pressed on a tablet press in the customary manner:
- 40 mg of substance from Example 4
- 120 mg of corn starch
- 13.5 mg of gelatin
- 45 mg of lactose
- 2.25 mg of Aerosil® (chemically pure silicic acid in submicroscopically fine dispersion)
- 6.75 mg of potato starch (as a 6% paste)

B) Sugar-Coated Tablets

- 20 mg of substance from Example 4
- 60 mg of core composition
- 70 mg of saccharification composition The core composition consists of 9 parts of corn starch, 3 parts of lactose and 1 part of 60:40 vinylpyrrolidone/vinyl acetate copolymer. The saccharification composition consists of 5 parts of cane sugar, 2 parts of corn starch, 2 parts of calcium carbonate and 1 part of talc. The sugar-coated tablets which had been prepared in this way are subsequently provided with a gastric juice-resistant coating.

IV. Biological Investigations

1. Receptor Binding Studies:

The substance to be tested was either dissolved in methanol/Chremophor® (BASF-AG) or in dimethyl sulfoxide and then diluted with water to the desired concentration.

Dopamine $D_3$ receptor:

The assay mixture (0.250 ml) was composed of membranes derived from ~$10^6$ HEK-293 cells possessing stably expressed human dopamine $D_3$ receptors, 0.1 nM $[^{125}I]$-iodosulpride and incubation buffer (total binding) or, in addition, test substance (inhibition curve) or 1 μM spiperone (nonspecific binding). Each assay mixture was run in triplicate.

The incubation buffer contained 50 mM tris, 120 mM NaCl, 5 mM KCl, 2 mM $CaCl_2$, 2 mM $MgCl_2$ and 0.1% bovine serum albumin, 10 μM quinolone and 0.1% ascorbic acid (prepared fresh daily). The buffer was adjusted to pH 7.4 with HCl.

Dopamine $D_{2L}$ receptor:

The assay mixture (1 ml) was composed of membranes from ~$10^6$ HEK-293 cells possessing stably expressed human dopamine $D_{2L}$ receptors (long isoform) and 0.01 nM $[^{125}I]$ iodospiperone and incubation buffer (total binding) or, in addition, test substance (inhibition curve) or 1 μM haloperidol (nonspecific binding). Each assay mixture was run in triplicate.

The incubation buffer contained 50 mM tris, 120 mM NaCl, 5 mM KCl, 2 mM $CaCl_2$, 2 mM $MgCl_2$ and 0.1% bovine serum albumin. The buffer was adjusted to pH 7.4 with HCl.

Measurement and Analysis:

After having been incubated at 25° C. for 60 minutes, the assay mixtures were filtered through a Wathman GF/B glass fiber filter under vacuum using a cell collecting device. The filters were transferred to scintillation viols using a filter transfer system. After 4 ml of Ultima Gold® (Packard) have been added, the samples were shaken for one hour and the radioactivity was then counted in a Beta-Counter (Packard, Tricarb 2000 or 2200CA). The cpm values were converted into dpm using a standard quench series and the program belonging to the instrument.

The inhibition curves were analyzed by means of iterative nonlinear regression analysis using the Statistical Analysis System (SAS) which is similar to the "LIGAND" program described by Munson and Rodbard.

In these tests, the compounds according to the invention exhibit very good affinities for the $D_3$ receptor ($K_i$<10 nM, frequently <5 nM) and bind selectively to the $D_3$ receptor.

The results of the binding tests are given in table 2, along with results obtained using two reference compounds A and B deemed representative of previously-described triazole compounds. The relative $D_3$ and $D_2$ affinities demonstrate the high selectivity of the compounds of the invention for the $D_3$ receptor.

2. Determination of the Concentration of Compounds in Plasma and Brain Following Dosing of Compounds in Animals Male Sprague-Dawley rats were used in this study (2 to 4 per experiment). The animals were fasted overnight prior to dosing and throughout the duration of the study but were permitted water ad libitum.

Each rat received a 10 mg/kg (5 mL/kg) dose orally by gavage. At 0.5, 3 and 8 hours after drug administration, three animals were put under deep anesthesia using isoflurane and euthanized by bleeding (cardiac puncture) under deep isoflurane anesthesia. EDTA blood samples and brain tissue will be collected from each rat. Upon collection, the samples were promptly placed in an ice bath, and within 2 hours after sample collection, the blood was centrifuged at about 4° C. The resulting brain and plasma samples were placed in clean glass tubes and stored in a freezer until analysis.

The plasma samples were assayed for parent compound using appropriate liquid chromatography—mass spectrometry procedures. The results for compounds I are given in tables 2, and illustrate the high brain concentrations attainable with the compounds of the invention.

TABLE 5

Properties of Compounds of the Formula I where Ar is Ar-1

| Ex. # | $R^1$ | n | $R^2$ | $K_i$ $D_3$ [nM] | Selectivity $[K_i(D_2)/K_i(D_3)]$ | Brain level [ng/g] |
|---|---|---|---|---|---|---|
| 1 | methyl | 1 | tert-butyl (racemate) | 19.5 | 26 | 1670 |
| 2 | hydrogen | 2 | cyclobutyl | 52 | 14 | n.d. |
| 3 | hydrogen | 1 | cyclobutyl | 12 | 44 | n.d. |
| 4 | methyl | 2 | Tert-butyl | 6.1 | 34 | 1920 |
| 5 | ethyl | 1 | n-propyl | 38 | 37 | n.d. |
| 6 | methyl | 1 | 1-methyl-cyclopropyl | 28.7 | 20 | n.d. |
| 8 | methyl | 1 | n-propyl | 56 | 33 | n.d. |
| 9 | methyl | 2 | n-propyl | 18.3 | 45 | n.d. |
| 10 | methyl | 2 | 1-methyl-cyclopropyl | 7.8 | 37 | n.d. |
| 12 | ethyl | 2 | n-propyl | 12.8 | 55 | n.d. |
| 13 | methyl | 1 | tert-butyl (enantiomer 1) | n.d. | n.d. | n.d. |
| 14 | methyl | 1 | tert-butyl (enantiomer 2) | n.d. | n.d. | n.d. |
| 15 | 4-fluoro-phenyl | 1 | trifluoromethyl | 12.6 | 100 | n.d. |
| 16 | 4-fluoro-phenyl | 2 | trifluoromethyl | 17.7 | 56 | n.d. |

TABLE 6

Binding properties of Compounds of the Formula I, Examples 17 to 31

| Exp. # | $k_i$ $D_3$ [nM] | Selectivity $[K_i(D_2)/K_i(D_3)]$ | Brain level [ng/g] |
|---|---|---|---|
| 17 | 5.95 | 53 | n.d. |
| 18 | 25 | 17 | n.d. |
| 19 | 32 | 17 | n.d. |
| 20 | 26.2 | 8 | n.d. |
| 21 | 16.6 | 18 | n.d. |
| 22 | 47.4 | 19 | n.d. |
| 23 | 59.8 | 49 | n.d. |
| 24 | 7.5 | 20 | n.d. |
| 25 | 23.3 | 30 | n.d. |
| 26 | 44.6 | 33 | n.d. |
| 27 | 9.7 | 24 | n.d. |
| 28 | 9.9 | 158 | n.d. |
| 29 | 20.3 | 59 | n.d. |
| 30 | 3.5 | 51 | n.d. |
| 31 | 22.6 | 37 | n.d. | n.d. = not determined
Exp.: Example

In the receptor binding studies described in IV.1 the compounds II of examples c.3, c.4, c.6, c.7, c.12, c.15, c.16, c.17, c18, c20, c.21, c.27, c.28 and c.29 showed $K_i$ $D_3$ values below 5 nM and selectivities [$K_i(D_2)/K_i(D_3)$] exceeding 50.

The brain levels determined for compounds c.9, c.16, c.17 and c.19 by the method described in IV.2 exceed 200 ng/g.

TABLE 7

Properties of Compounds of the Formula IIa

| Exp. # | $D_3$ [nM] | $D_2/D_3$ | Brain level [ng/g] |
|---|---|---|---|
| c. 4 | 1.5 | 96 | 290 |
| c. 7 | 1.2 | 115 | n.d. |
| c. 11 | 1.7 | 470 | 840 |
| c. 12 | 2.4 | 143 | 780 |
| c. 13 | 1.3 | 157 | n.d. |
| c. 14 | 1.5 | 135 | n.d. |
| c. 15 | 2 | 364 | 1410 |
| c. 16 | 0.65 | 237 | n.d. |
| c. 17 | 0.9 | 293 | n.d. |
| c. 18 | 2.9 | 134 | n.d. |
| c. 45 | 3.9 | 21 | |
| c. 46 | 3.75 | 25 | |
| c. 48 | 1.2 | 4 | |
| c. 50 | 0.46 | 18 | |
| c. 53 | 1.1 | 5 | |
| c. 54 | 1.46 | 88 | | n.d. not determined
Exp.: Example

We claim:
1. A triazole compound of formula

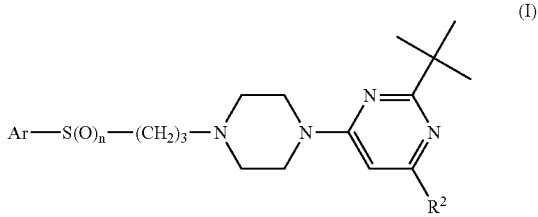

wherein
n is 1 or 2;

Ar is a C-bound 1,2,4-triazol radical which carries a radical $R^1$ on the remaining carbon atom and a radical $R^{1a}$ on one of the nitrogen atoms;

$R^1$ is hydrogen, $C_1$-$C_6$ alkyl, $C_3$-$C_6$ cycloalkyl, $C_1$-$C_4$ alkoxymethyl, fluorinated $C_1$-$C_6$ alkyl, fluorinated $C_3$-$C_6$ cycloalkyl, fluorinated $C_1$-$C_4$ alkoxymethyl, phenyl or 5- or 6-membered heteroaryl, wherein phenyl and heteroaryl may be unsubstituted or substituted by 1, 2, 3 or 4 radicals $R^a$ selected independently of each other from halogen, $C_1$-$C_6$ alkyl, $C_3$-$C_6$ cycloalkyl, $C_1$-$C_4$ alkoxy-$C_1$-$C_4$-alkyl, fluorinated $C_1$-$C_4$ alkyl, CN, $NO_2$, $OR^3$, $NR^3R^4$, $C(O)NR^3R^4$, O—$C(O)NR^3R^4$, $SO_2NR^3R^4$, $COOR^5$, $SR^6$, $SOR^6$, $SO_2R^6$, O—$C(O)R^7$, $COR^7$ or $C_3$-$C_5$ cycloalkylmethyl, wherein phenyl and heteroaryl may also carry a phenyl group or an aromatic 5- or 6-membered C-bound heteroaromatic radical, comprising 1 nitrogen atom as ring member and 0, 1, 2 or 3 further heteroatoms, independently of each other, selected from O, S and N, wherein the last two mentioned radicals may carry 1, 2, 3 or 4 of the aforementioned radicals $R^a$—;

$R^{1a}$ is hydrogen or $C_1$-$C_4$ alkyl;

$R^2$ is $C_1$-$C_6$ alkyl, $C_3$-$C_6$ cycloalkyl, fluorinated $C_1$-$C_6$ alkyl or fluorinated $C_3$-$C_6$ cycloalkyl;

$R^3$, $R^4$, $R^5$, $R^6$, and $R^7$ independent of each other are H, $C_1$-$C_6$ alkyl, optionally substituted with OH, $C_1$-$C_4$ alkoxy or phenyl, $C_1$-$C_4$ haloalkyl or phenyl, which may carry 1, 2 or 3 radicals selected from the group consisting of $C_1$-$C_6$ alkyl, $C_1$-$C_6$ alkoxy, $NR^{3a}R^{4a}$, CN, $C_1$-$C_2$ fluoroalkyl and halogen, wherein $R^{3a}$ and $R^{4a}$ are independent of each other H, $C_1$-$C_6$ alkyl, optionally substituted with OH, $C_1$-$C_4$ alkoxy or phenyl, $C_1$-$C_4$ haloalkyl or phenyl, which may carry 1, 2 or 3 radicals selected from the group consisting of $C_1$-$C_6$ alkyl, $C_1$-$C_6$ alkoxy, amino, $NH(C_1$-$C_4$ alkyl) and $N(C_1$-$C_4$ alkyl)$_2$;

$R^4$ may also be a radical $COR^8$, wherein $R^8$ is hydrogen, $C_1$-$C_6$ alkyl, $C_1$-$C_6$ alkoxy or phenyl, which may carry 1, 2 or 3 radicals selected from the group consisting of $C_1$-$C_6$ alkyl, $C_1$-$C_6$ alkoxy, $NR^3R^4$, CN, $C_1$-$C_2$ fluoroalkyl and halogen, $R^3$ and $R^4$ may together with the nitrogen atom to which they are bound form a N-bound 5 or 6 membered saturated heterocycle, which may comprise an oxygen atom or an additional nitrogen atom as a ring member and which may carry 1, 2, 3 or 4 $C_1$-$C_6$ alkyl groups, or physiologically tolerated acid addition salts thereof.

2. The compound as claimed in claim 1, wherein Ar is a radical of the formula Ar-1,

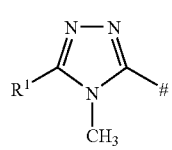

(Ar-1)

wherein # denotes the binding position to the sulfur atom of the group S(O)n and $R^1$ is as defined in claim 1.

3. The compound as claimed in claim 1, wherein Ar is a radical of the formula Ar-2,

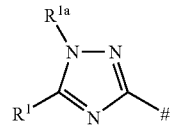

(Ar-2)

wherein # denoted the binding position of the sulfur atom of the group S(O)n and $R^1$ and $R^{1a}$ are as defined in claim 1.

4. The compound as claimed in claim 1, wherein Ar is a radical of the formula Ar-3,

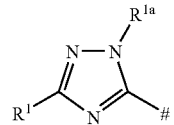

(Ar-3)

wherein # denoted the binding position of the sulfur atom of the group S(O)n and $R^1$ and $R^{1a}$ are as defined in claim 1.

5. The compound as claimed in claim 1, wherein $R^1$ is selected from the group consisting of hydrogen, $C_1$-$C_4$ alkyl, $C_3$-$C_5$ cycloalkyl, $C_1$-$C_4$ alkoxymethyl and trifluoromethyl.

6. The compound as claimed in claim 1, wherein $R^1$ is hydrogen or methyl.

7. The compound as claimed in claim 1, wherein $R^2$ is selected from the group consisting of $C_3$-$C_4$ alkyl or fluorinated $C_1$-$C_2$ alkyl.

8. The compound as claimed in claim 1, wherein $R^2$ is selected from the group consisting of n-propyl, isopropyl and tert-butyl.

9. The compound as claimed in claim 1, wherein $R^2$ is tert-butyl.

10. The compound as claimed in claim 9, wherein $R^1$ is hydrogen.

11. The compound as claimed in claim 9, wherein $R^1$ is methyl.

12. The compound as claimed in claim 1, wherein $R^2$ is selected from the group consisting of trifluoromethyl and difluoromethyl.

13. The compound as claimed in claim 1, wherein $R^2$ is trifluorormethyl.

14. The compound as claimed in claim 13, wherein $R^1$ is hydrogen.

15. The compound as claimed in claim 13, wherein $R^1$ is methyl.

16. The compound as claimed in claim 1, wherein $R^2$ is $C_3$-$C_4$ cycloalkyl or fluorinated $C_3$-$C_4$ cycloalkyl.

17. The compound as claimed in claim 16, wherein $R^1$ is hydrogen.

18. The compound as claimed in claim 16, wherein $R^1$ is methyl.

19. A pharmaceutical composition comprising one or more compounds as claimed in claim 1 together with at least one physiologically acceptable carrier or auxiliary substance.

20. A method for treating a medical disorder selected from Parkinson's disease, schizophrenia, cognitive disturbances, depression, anxiety, addiction, kidney function disturbances and eating disturbances, said method comprising administering an effective amount of one or more compounds as claimed in claim 1 to a subject in need thereof.

21. The method as claimed in claim 20, wherein the medical disorder is schizophrenia.

* * * * *